(12) United States Patent
Stährfeldt et al.

(10) Patent No.: US 6,420,461 B1
(45) Date of Patent: Jul. 16, 2002

(54) COMPOUNDS BASED ON POLYALKYL-1-OXADIAZASPIRODECANE COMPOUNDS

(75) Inventors: Thomas Stährfeldt, Weil am Rhein; Mathias Mehrer, Gablingen; Matthias Zäh, Gersthofen; Gerhard Pfahler, Eichenau, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/423,759

(22) PCT Filed: May 11, 1998

(86) PCT No.: PCT/EP98/02738

§ 371 (c)(1),
(2), (4) Date: Nov. 12, 1999

(87) PCT Pub. No.: WO98/51690

PCT Pub. Date: Nov. 19, 1998

(30) Foreign Application Priority Data

May 13, 1997 (DE) .......................................... 197 19 944

(51) Int. Cl.⁷ ............................. C08K 5/34; B86D 5/06
(52) U.S. Cl. .......................... 524/95; 524/91; 524/99; 524/100; 524/102; 524/111; 524/117; 524/128; 524/151; 524/120; 524/126; 524/247; 524/359; 524/399; 524/432; 524/434; 524/433; 252/400.2; 252/400.24; 252/400.52; 252/401; 252/403; 546/189
(58) Field of Search .................. 252/400.2, 400.24, 252/400.52, 401, 403; 524/95, 91, 100, 102, 111, 117, 128, 151, 120, 126, 247, 359, 399, 432, 434, 433; 546/189

(56) References Cited

U.S. PATENT DOCUMENTS

| | | | |
|---|---|---|---|
| 4,233,412 A | 11/1980 | Rody et al. ................. 525/167 |
| 4,299,926 A | 11/1981 | Rody et al. | |
| 4,325,863 A | 4/1982 | Hinsken et al. ............. 624/111 |
| 4,338,244 A | 7/1982 | Hinsken et al. ............. 524/109 |
| 4,340,534 A | 7/1982 | Weizer et al. | |
| 4,405,735 A | 9/1983 | Wiezer et al. | |
| 4,477,615 A | 10/1984 | Raspanti et al. ............ 524/100 |
| 4,529,760 A | 7/1985 | Leistner et al. ............ 524/102 |
| 4,692,486 A | 9/1987 | Gugumus ................... 524/100 |
| 4,838,943 A | 6/1989 | Bitterli et al. .............. 106/400 |
| 4,857,595 A | 8/1989 | Kazmierzak et al. ....... 525/142 |
| 4,863,981 A | 9/1989 | Gugumus ................... 524/97 |
| 4,929,652 A | 5/1990 | Gugumus ................... 524/91 |
| 5,037,870 A | 8/1991 | Gugumus ................... 524/102 |
| 5,134,181 A | 7/1992 | Masina ...................... 524/100 |
| 5,169,925 A | 12/1992 | Schmailzl et al. | |
| 5,175,312 A | 12/1992 | Dubs et al. ................. 549/307 |
| 5,180,762 A | 1/1993 | Canova ...................... 524/100 |
| 5,216,052 A | 6/1993 | Nesvadba et al. .......... 524/108 |
| 5,252,643 A | 10/1993 | Nesvadba ................... 524/111 |
| 5,356,966 A | 10/1994 | Nesvadba ................... 524/111 |
| 5,367,008 A | 11/1994 | Nesvadba ................... 524/111 |
| 5,369,159 A | 11/1994 | Nesvadba ................... 524/111 |
| 5,371,263 A | 12/1994 | Quotschalla et al. ........ 558/71 |
| 5,428,162 A | 6/1995 | Nesvadba ................... 544/221 |
| 5,428,177 A | 6/1995 | Nesvadba ................... 549/304 |
| 5,550,234 A | 8/1996 | Gaa et al. | |
| 5,633,378 A | 5/1997 | Gaa et al. ................... 546/16 |
| 5,719,217 A | 2/1998 | Gugumus ................... 524/100 |

FOREIGN PATENT DOCUMENTS

| | | |
|---|---|---|
| DE | 262 439 | 7/1913 |
| DE | 27 19 131 | 12/1977 |
| DE | 44 23 055 A1 | 1/1996 |
| EP | 0 028 318 | 5/1981 |
| EP | 0 057 885 | 8/1982 |
| EP | 0 093 693 | 11/1983 |
| EP | 0 143 464 A2 | 6/1988 |
| EP | 0 278 578 A2 | 8/1988 |
| EP | 0 343 717 | 11/1989 |
| EP | 0 359 276 A2 | 3/1990 |
| EP | 0 400 454 A2 | 12/1990 |
| EP | 0 402 889 | 12/1990 |
| EP | 0 429 731 A2 | 6/1991 |
| EP | 0 517 658 A1 | 12/1992 |
| EP | 0 558 040 A2 | 9/1993 |
| EP | 0 567 117 A1 | 10/1993 |
| EP | 0 612 816 A1 | 8/1994 |
| EP | 0 632 092 A1 | 1/1995 |
| EP | 0 690 060 | 1/1996 |
| EP | 0 690 094 A1 | 1/1996 |
| EP | 0 709 426 A2 | 5/1996 |
| EP | 0 723 990 A1 | 7/1996 |

OTHER PUBLICATIONS esp@cenet abstract for DE 4239437.

(List continued on next page.)

Primary Examiner—Kriellion Sanders
(74) Attorney, Agent, or Firm—Susan S. Jackson; Scott E. Hanf

(57) ABSTRACT

The present invention relates to novel compounds of the formula (III)

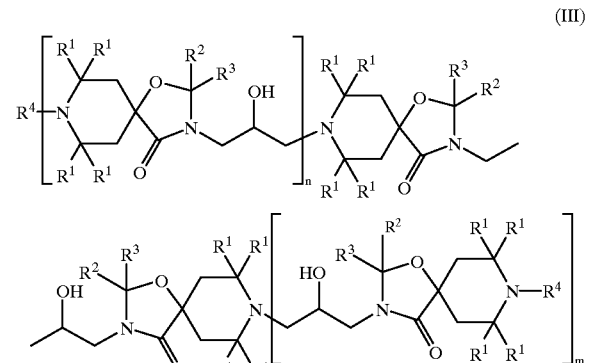

in which the substituents are as defined in the description, to a process for their preparation and to mixtures with other compounds. The compounds of the formula (III) are suitable for stabilizing organic material against the effect of light and heat.

36 Claims, No Drawings

OTHER PUBLICATIONS esp@cenet abstract for DE 4411369.
esp@cenet abstract for DE 4418080.
esp@cenet abstract for DE 19537140.
esp@cenet abstract for EP 0576833.
esp@cenet abstract for EP 0612792.
esp@cenet abstract for EP 0665294.
esp@cenet abstract for EP 0676405.

C. Ferri, Reaktionen der organischen Synthese, 1978, p. 504.
Houben–Weyl, vol. VI/3, p. 456 or vol. XI/1, p. 311.
Research Disclosure Jan. 1993, No. 34549.
Derwent 89–122 89–122 983/17.
Chemical Abstracts 111:58 964u.
Derwent 94–177 274/22.
Chemical Abstracts–CAS No. 136 504–96–6.

COMPOUNDS BASED ON POLYALKYL-1-OXADIAZASPIRODECANE COMPOUNDS

Stabilizing polymeric material against the destructive influence of high-energy radiation is the subject of intense research efforts. In recent years, a large number of light stabilizers based on sterically hindered amines has been developed which ensure the stabilization of polymeric material in an outstanding manner. Nevertheless, low molecular mass stabilizers of this class of substance, in particular, suffer from the disadvantage of their ready extractability and high volatility from the polymer material to be stabilized, so that following a certain period of use there is unwanted breakdown of the material. For this reason, a considerable number of polymeric stabilizers based on sterically hindered amines have been prepared, which possess said disadvantages to a lesser degree if at all. By way of example there may be mentioned stabilizers as described, for instance, in EP-A-93693, DE-A-2719131, EP-A-343717 and EP-A-402889. However, there is a constant demand for new, more effective stabilizers which possess improved photoprotective or additional, better performance properties.

EP-A-28318 describes the preparation and polymerization, and EP-A-402889 the improved polymerization, of compounds of the formula

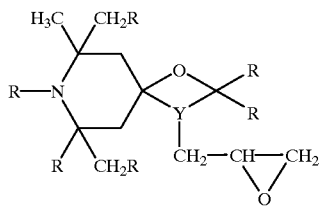

to form oligomeric and, respectively, polymeric stabilizers, while German Patent Application No. 19608163.7 describes an effective, high-yielding and eco-friendly method of preparing such stabilizers.

European Patent Application 95 109 777.3 and EP-A-57885 (cf. Example 11 therein) describe derivatives of compounds of the formula

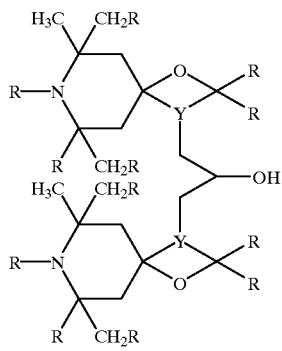

which constitute new and effective light stabilizers.

It has surprisingly now been found that reaction of compounds of the formula (I) with compounds of the formula (II)

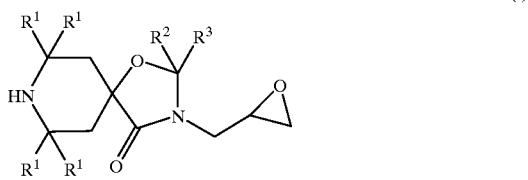

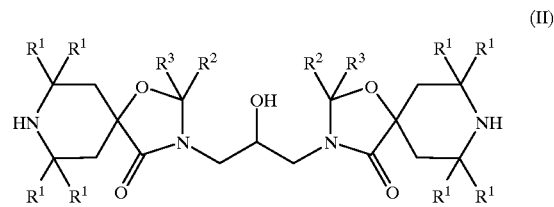

produces new stabilizers of the formula (III).

The invention therefore provides novel compounds of the formula (III)

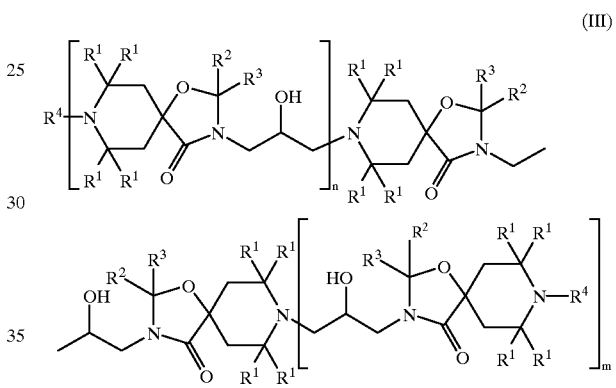

in which n and m independently of one another are a number from 0 to 100, but n and m cannot both be 0, $R^1$ is hydrogen, $C_5$–$C_7$-cycloalkyl, or a $C_1$–$C_{12}$-alkyl group, $R^2$ and $R^3$ independently of one another are a hydrogen atom or a $C_1$–$C_{18}$-alkyl group or, together with the carbon atom connecting them, are a 5- to 13-membered ring or, together with the carbon atom connecting them, are a group of the formula (IV)

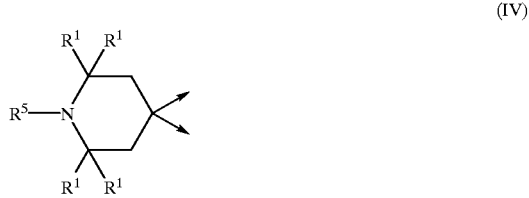

$R^4$ and $R^5$ independently of one another are either hydrogen or a $C_1$–$C_{22}$-alkyl group,
an oxygen radical O*, —OH, —NO, —CH$_2$CN, benzyl, allyl, a $C_1$–$C_{30}$-alkyloxy group, a $C_5$–$C_{12}$-cycloalkyloxy group, a $C_6$–$C_{10}$-aryloxy group in which additionally the aryl radical may also be substituted, a $C_7$–$C_{20}$-arylalkyloxy group in which additionally the aryl radical may also be substituted, a $C_3$–$C_{10}$-alkenyl group, a $C_3$–$C_6$-alkynyl group, a $C_1$–$C_{10}$-acyl group, halogen or $C_7$–$C_9$-phenylalkyl which is unsubstituted or substituted on the phenyl ring by $C_1$–$C_4$-alkyl.

Also highly suitable are compounds of the formula (III) in which n and m independently of one another are a number from 0 to 10, but n and m cannot both be 0, $R^1$ is hydrogen, $C_6$-cycloalkyl, or a $C_1$–$C_4$-alkyl group, $R^2$ and $R^3$ independently of one another are a hydrogen atom or a $C_1$–$C_8$-alkyl group, or, together with the carbon atom connecting them, are a 6- to 12-membered ring or, together with the carbon atom connecting them, are a group of the formula (IV), $R^4$ and $R^5$ independently of one another are either hydrogen or a $C_1$–$C_5$-alkyl group, an oxygen radical O*, —OH, —NO, —CH$_2$CN, benzyl, allyl, a $C_1$–$C_{10}$-alkyloxy group, a $C_5$–$C_6$-cycloalkyloxy group, a $C_6$–$C_7$-aryloxy group in which additionally the aryl radical can also be substituted, a $C_7$–$C_{10}$-arylalkyloxy group in which additionally the aryl radical can also be substituted, a $C_3$–$C_6$-alkenyl group, a $C_3$–$C_6$-alkynyl group, a $C_1$–$C_4$-acyl group, halogen or $C_7$–$C_9$-phenylalkyl which is unsubstituted or substituted on the phenyl ring by $C_1$–$C_2$-alkyl.

Particularly preferred compounds of the formula (III) are those in which n and m independently of one another are a number from 0 to 5, but n and m cannot both be 0, $R^1$ is methyl, $R^2$ and $R^3$, together with the carbon atom connecting them, are a 12-membered ring or, together with the carbon atom connecting them, are a group of the formula (IV), $R^4$ and $R^5$ independently of one another are hydrogen, methyl, acetyl, octyloxy or cyclohexyloxy.

The invention also relates to a general process for the preparation of compounds of the formula (III), and to their use for stabilizing organic material, and to an organic, preferably polymeric material stabilized with compounds of the formula (III), said material being selected in particular from plastics, coating compositions, lacquers and oils or their precursors.

The preparation of compounds of the formula (III) where $R^4$=hydrogen is carried out by reacting compounds of the formula (I) with compounds of the formula (II). To prepare (III) it is possible to employ processes already known per se, as are described, for example, in C. Ferri, *Reaktionen der organischen Synthese*, 1978, page 504 or *Houben-Weyl*, Vol. VI/3, page 456 or Vol. XI/1, page 311. The reaction can be carried out with or without solvents; suitable solvents are preferably high-boiling, aprotic solvents, such as toluene, xylene, mesitylene or decalin, for example. The reaction can be implemented with or without catalyst (especially by thermal means), with suitable catalysts being bases, preferably metal salts, especially alkali metal hydroxides, such as NaOH or KOH, for example. A preferred preparation process is the reaction of (I) and (II) directly in bulk, without using a solvent and without catalyst. In this case (I) and (II) are polymerized in a molar ratio in the range from 1:1 (equimolar) to 100:1 in the temperature range from 100 to 300° C., preferably from 120 to 250° C. and, in particular, from 160 to 220° C., preferably in the absence of oxygen. A solventless polymerization in vacuo is particularly suitable. The product in this case, after working up, is a solid, colorless, amorphous resin. The molecular weight of the resulting oligomer or polymer can be controlled as a function of the temperature, the molar ratio in which the starting materials are employed, and/or the reaction time. Methods for subsequent modification of $R^4$ ($R^4$ other than hydrogen) are sufficiently well known from the prior art; for example, from EP-A-0 705 896 or from EP-A-0 690 060. Of outstanding importance in particular are the derivatives of the compound (III) where $R^4$=H or $R^4$=methyl.

The compounds of the invention are outstandingly suitable for stabilizing organic material against the action of light, oxygen and heat. They can be added to the organic material to be stabilized, prior to, during or after polymerization, in solid form, as a melt, as a solution in solvents or else as a masterbatch. The solutions may comprise the new stabilizer, for example, in 5–80% concentrations; a masterbatch is particularly appropriate if it comprises the new stabilizer in a concentration of from 1 to 80%, but preferably 5–30%, with the remainder of the masterbatch comprising a polymer compatible with the polymer to be stabilized. Both the solution and the masterbatch may additionally include other stabilizers or effect substances, examples being UV absorbers, antioxidants, pigments, acid scavengers or fillers. The new stabilizers are preferably employed such that their concentration in the polymer to be stabilized is from 0.001 to 5% by weight, preferably from 0.02 to 2% by weight, based on the organic material, and they are present either alone or in combination with further additives. The term organic material embraces, for example, precursors for plastics, coating materials, lacquers and oils, but especially the plastics, coating materials, lacquers and oils themselves.

The compounds of the formula (III) are particularly suitable for stabilizing films, fibers, tapes, multifilaments, fabrics, extruded, blow-molded, injection molded and thermoformed articles, powder coating materials, printing inks, toner inks, photographic material, pigments, wood stains, leathers, architectural paints, protective coatings for steel structures, lubricating oils, machine oils, bitumen or asphalt and for stabilizing compounds which have a tendency to undergo spontaneous polymerization.

The compounds of the formula (III) of the invention can also be employed, advantageously, in combinations with further stabilizers. The result of these new combinations are mixtures having an improved profile of properties with respect to the individual components, such as synergy in the photoprotective effect, for example.

Combining the compounds of the formula (III) with monomeric HALS stabilizers in a weight ratio of from 10:1 to 1:10 is particularly advantageous. Combinations of polymeric with monomeric HALS stabilizers are described, for instance, in EP-A-80431 and EP-A-632092. It is particularly advantageous to combine, in accordance with the invention, (III) with compounds of the formulae A1 to A10.

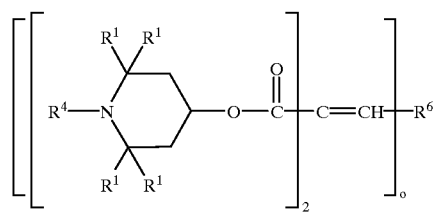

A1 in which

R¹ and R⁴ are as defined above,

R⁶ is an aromatic radical substituted one or more times by hydrogen, $C_1$–$C_4$-alkyl, $C_1$–$C_4$-alkoxy, halogen, cyano, carboxyl, nitro, amino, $C_1$–$C_4$-alkylamino, $C_1$–$C_4$-dialkylamino, or acyl, o is 1 or 2,

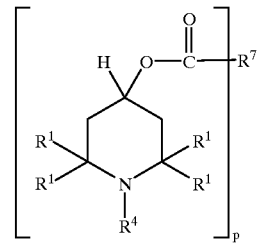

A2 in which

R¹ and R⁴ are as defined in claim 1, p=1 or 2 and if p=1,

R⁷ is $C_1$–$C_{22}$-alkyl, $C_2$–$C_{18}$-oxaalkyl, $C_2$–$C_{18}$-thiaalkyl, $C_2$–$C_{18}$-azaalkyl or $C_2$–$C_8$-alkenyl;

if p=2,

R⁷ is $C_1$–$C_{22}$-alkylene, $C_2$–$C_{18}$-oxaalkylene, $C_2$–$C_{18}$-thiaalkylene, $C_2$–$C_{18}$-azaalkylene or $C_2$–$C_8$-alkenylene;

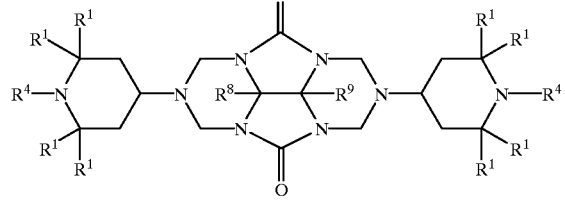

A3 in which

R¹ and R⁴ are as defined in claim 1,

R⁸ and R⁹ independently of one another are hydrogen, $C_1$–$C_6$-alkyl, $C_7$–$C_{12}$-aralkyl, -aryl or carboxylic ester, R⁸ and R⁹ together are a tetra- or pentamethyl group;

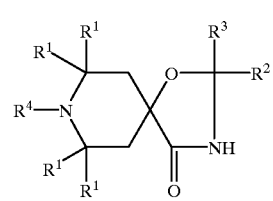

A4

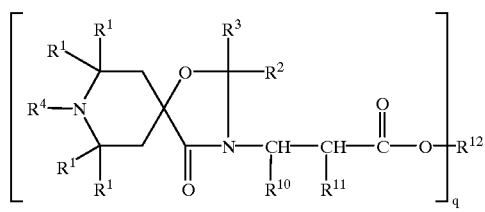

A5 in which

R¹, R², R³ and R⁴ are as defined in claim 1, q is a number 1 or 2,

R¹⁰ is hydrogen, methyl, phenyl or carb-$C_1$–$C_{21}$-alkoxy,

R¹¹ is hydrogen or methyl,

R¹², if q=1, is hydrogen, $C_1$–$C_{21}$-alkyl, $C_2$–$C_{22}$-alkenyl, $C_5$–$C_{12}$-cycloalkyl, a radical of the formula

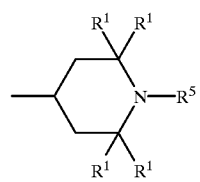

where

R¹ and R⁵ are as defined in claim 1, and

R¹², if q=2, is $C_1$–$C_{18}$-alkylene, $C_5$–$C_9$-cycloalkylene or arylene;

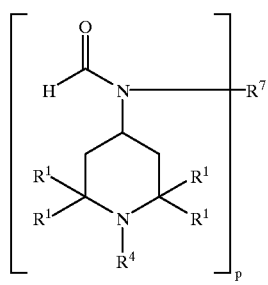

A6 where R¹, R⁴, R⁷ and p are as defined above;

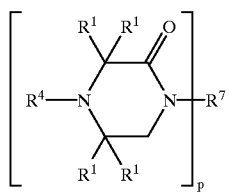

A7 where $R^1$, $R^4$, $R^7$ and p are as defined above;

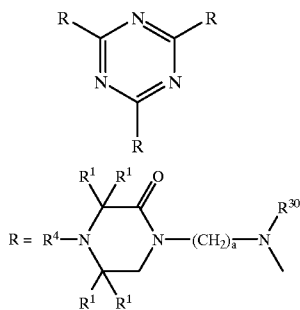

A8 where $R^1$, $R^4$ are as defined above,
$R^{30}$ is hydrogen, $C_1$–$C_{12}$-alkyl, $C_5$–$C_{12}$-cycloalkyl, phenyl or $C_7$–$C_9$-phenylalkyl, and
a is a number from 1 to 10;

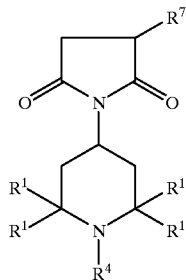

A9 where $R^1$ and $R^4$ are as defined above and $R^7$ is as defined for p=1 in the formula A2;

a product A10 obtainable by reacting a polyamine of the formula A10a with formula A10b:

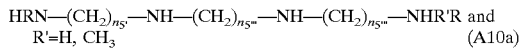

HRN—$(CH_2)_{n_{5'}}$—NH—$(CH_2)_{n_{5''}}$—NH—$(CH_2)_{n_{5'''}}$—NHR'R and R'=H, CH$_3$    (A10a)

(A10b)

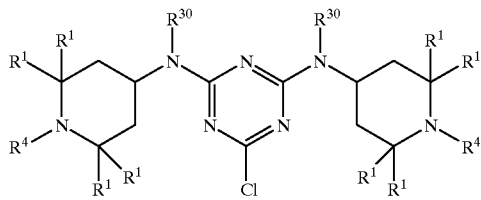

where
$R^1$, $R^4$ and $R^{30}$ are as defined above,
$n_{5'}$, $n_{5''}$ and $n_{5'''}$ independently of one another are a number from 2 to 12.

Preference is given to mixtures of compounds of the formula (III) with compounds of the formulae A1 to A10 in which
n and m independently of one another are a number from 0 to 10, but n and m cannot both be 0,
$R^1$ is hydrogen or a $C_1$–$C_4$-alkyl group,
$R^2$ and $R^3$ independently of one another are a hydrogen atom or a $C_1$–$C_8$-alkyl group or, together with the carbon atom connecting them, are a 6- to 12-membered ring or, together with the carbon atom connecting them, are a group of the formula (IV),
R and $R^5$ independently of one another are either hydrogen or a $C_1$–$C_5$-alkyl group, an oxygen radical O*, —OH, —NO, —CH$_2$CN, benzyl, allyl, a $C_1$–$C_{10}$-alkyloxy group, a $C_5$–$C_6$-cycloalkyloxy group, a $C_6$–$C_7$-aryloxy group in which additionally the aryl radical may also be substituted; a $C_7$–$C_{10}$-arylalkyloxy group in which additionally the aryl radical may also be substituted, a $C_3$–$C_6$-alkenyl group, a $C_3$–$C_6$-alkynyl group, a $C_1$–$C_4$-acyl group, halogen or $C_7$–$C_9$-phenylalkyl which is unsubstituted or substituted on the phenyl ring by $C_1$–$C_2$-alkyl,
$R^7$ is a straight-chain $C_1$–$C_{10}$-alkylene (if p=2); $C_1$–$C_{12}$-alkyl (if p=1)
$R^8$ and $R^9$ independently of one another are hydrogen, $C_1$–$C_2$-alkyl, $C_7$–$C_8$-arylalkyl, aryl- or carboxylic ester,
$R^{10}$ is hydrogen, methyl, phenyl or $C_1$–$C_2$-alkoxy,
$R^{11}$ is hydrogen or methyl,
$R^{12}$, if q=1, is hydrogen, $C_1$–$C_{16}$-alkyl, $C_2$–$C_{16}$-alkenyl, $C_5$–$C_6$-cycloalkyl, a radical of the formula

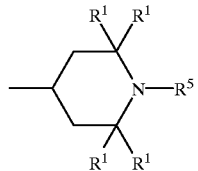

$R^{12}$, if q=2, is $C_1$–$C_{16}$-alkylene, $C_5$–$C_6$-cycloalkylene or arylene,
$R^{30}$ is hydrogen, $C_1$–$C_8$-alkyl, $C_5$–$C_7$-cycloalkyl, phenyl or $C_7$–$C_8$-phenylalkyl,
a is 1 to 5,
o 1 and
p 2 to 5.

Very particular preference is given to mixtures in which
n and m independently of one another are a number 0–5, but n and m cannot both be 0,
$R^1$ is methyl,
$R^2$ and $R^3$, together with the carbon atom connecting them, are a 12-membered ring or, together with the carbon atom connecting them, are a group of the formula (IV),
$R^4$ and $R^5$ independently of one another are hydrogen, methyl, acetyl, octyloxy or cyclohexyloxy,
$R^6$ is p-methoxyphenyl,
$R^7$ is octamethylene, hexamethylene or ethylene (if p=2), dodecyl (if p=1),
$R^8$ and $R^9$ are hydrogen,
$R^{10}$ is hydrogen,
$R^{11}$ is hydrogen,
$R^{12}$ is dodecamethylene or tetradecarnethylene,
$R^{30}$ is cyclohexyl or n-butyl,
a is 2,
o is 1,
p is 2
and q is 1.

The following compounds are especially suitable in a mixture with compounds of the formula (III):

A'1 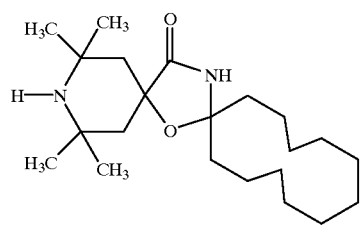
A'2 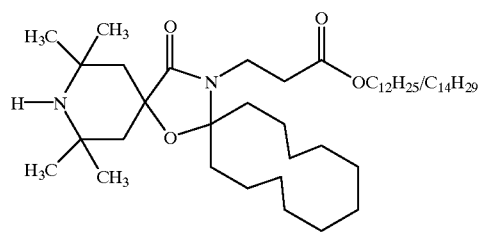
A'3 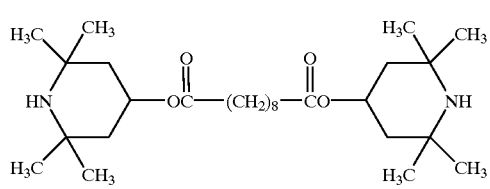
A'4 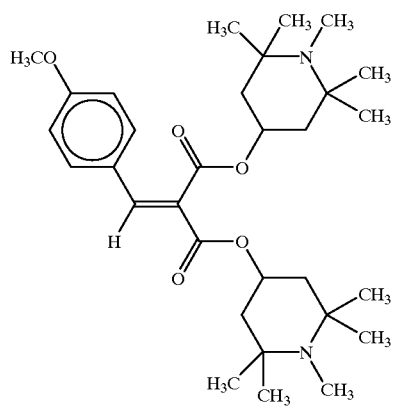
A'5 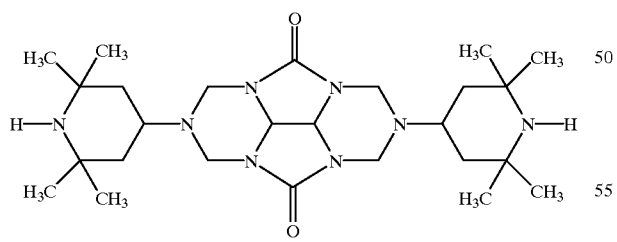
A'6 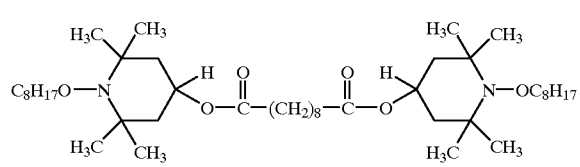
A'7 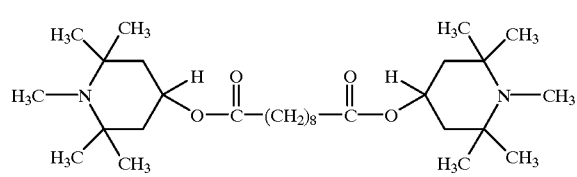
A'8 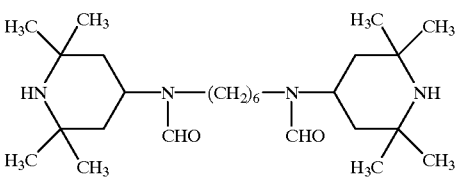
A'9 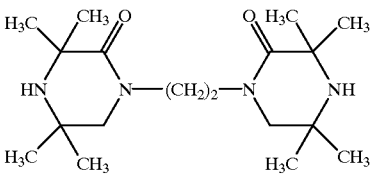
A'10
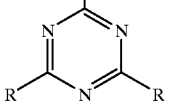
R = 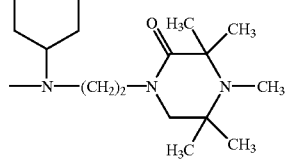
A'11 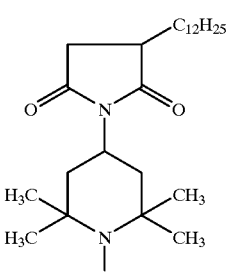
A'12 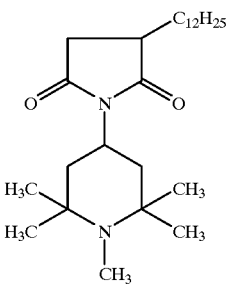

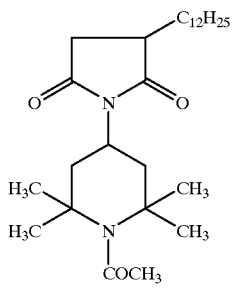
A'13

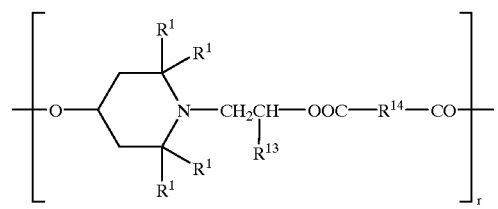
B1 in which $R^1$ is hydrogen, $C_5$–$C_7$-cycloalkyl or a $C_1$–$C_{12}$-alkyl group, $R^{13}$ is hydrogen or methyl, $R^{14}$ is a direct bond or $C_1$–$C_{10}$-alkylene and r is a number from 2 to 50;

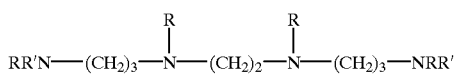
A'14

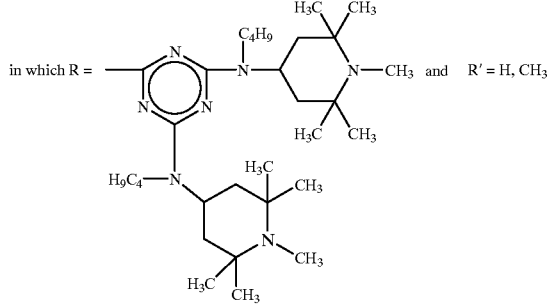

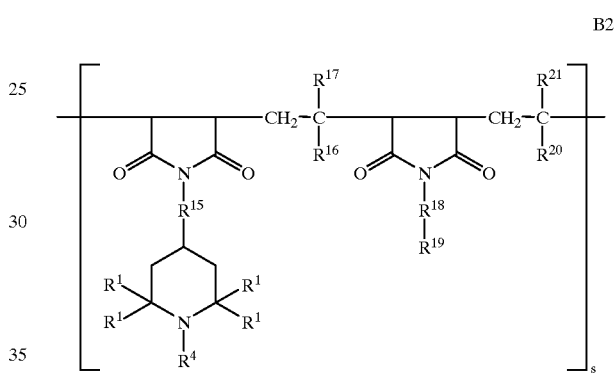
B2 where $R^1$ and $R^4$ are as defined for formula (III), $R^{15}$ and $R^{18}$ independently of one another are a direct bond or a group —N($R^{22}$)—CO—$R^{23}$—CO—N($R^{24}$)—, $R^{22}$ and $R^{24}$ independently of one another are hydrogen, $C_1$–$C_8$-alkyl, $C_5$–$C_{12}$-cyclolalkyl, phenyl, $C_7$–$C_9$-phenylalkyl, or a group of the formula A particularly suitable embodiment of the invention comprises mixtures of a compound of the formula (III) with one or more stabilizers based on sterically hindered amines, where the co-component(s) is (are) TINUVIN® 770, TINUVIN® 765, TINUVIN® 123, HOSTAVIN® N 20, HOSTAVIN® N 24, UVINUL® 4049, SANDUVOR® PR31, UNIVUL® 4050, GOODRITE® UV 3034 or GOODRITE® 3150, SANDUVOR® 3055, SANDUVOR® 3056, SANDUVOR® 3058, CHIMASSORB® 119 and CHIMASSORB® 905.

The compound of the formula (III) of the invention can also be employed advantageously with polymeric HALS stabilizers in a weight ratio of from 10:1 to 1:10. The result of these new combinations are mixtures which have an improved profile of properties with respect to the individual components; for example, synergy in the photoprotective effect. Combinations of polymeric HALS stabilizers are described, for example, in EP-A-252877, EP-A-709426, Research Disclosure January 1993 No. 34549, EP-A-723990.

A particularly preferred embodiment in this context comprises the combinations of the compound (III) with polymeric HALS compounds of the formulae B1 to B7:

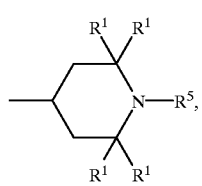
B2a $R^{23}$ is a direct bond or $C_1$–$C_4$-alkylene, $R^{16}$, $R^{17}$, $R^{20}$, $R^{21}$ independently of one another are hydrogen, $C_1$–$C_{30}$-alkyl, $C_5$–$C_{12}$-cycloalkyl, phenyl, or a group of the formula B2a, $R^{19}$ is hydrogen, $C_1$–$C_{30}$-alkyl, $C_5$–$C_{12}$-cycloalkyl, $C_7$–$C_9$-phenylalkyl, phenyl or a group of the formula B2a and s is a number from 1 to 50;

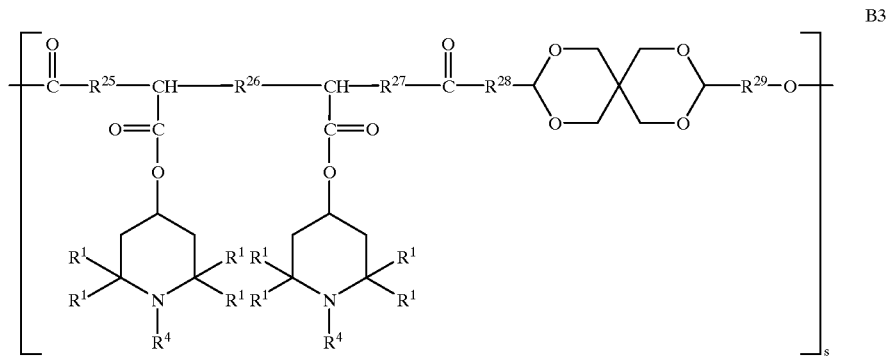

where

R$^1$, R$^4$ and s are as defined above,

R$^{25}$, R$^{26}$, R$^{27}$, R$^{28}$ and R$^{29}$ independently of one another are a direct bond or C$_1$–C$_{10}$-alkylene;

a product B4 obtainable by reacting a polyamine of the formula B4a with cyanuric chloride and then reacting the resulting product with a compound of the formula B4b,

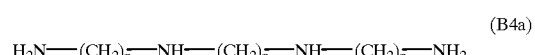

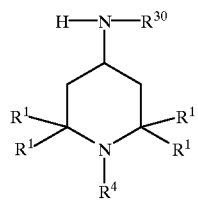

where
R$^1$ and R$^4$ are as defined for formula (III),
n$_{5'}$, n$_{5''}$ and n$_{5'''}$ independently of one another are a number from 2 to 12,
R$^{30}$ is as defined above; where B4 is a compound of the formula B4-1, B4-2, B4-3

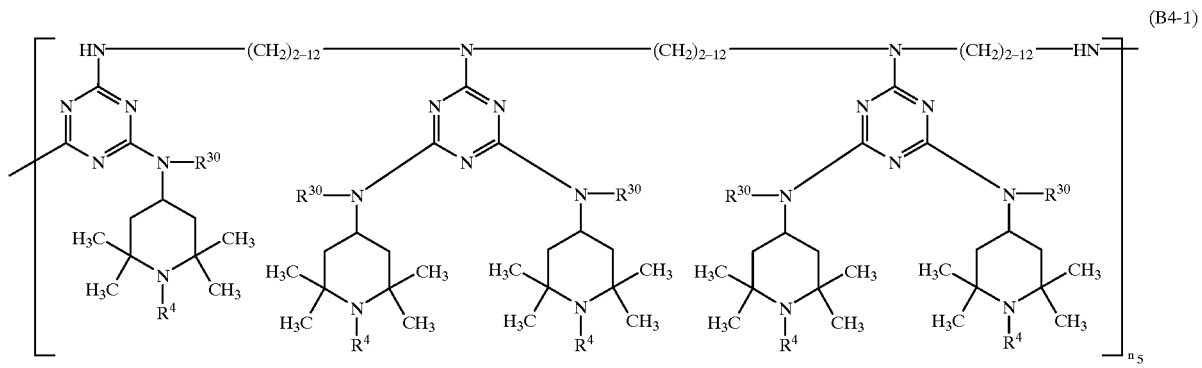

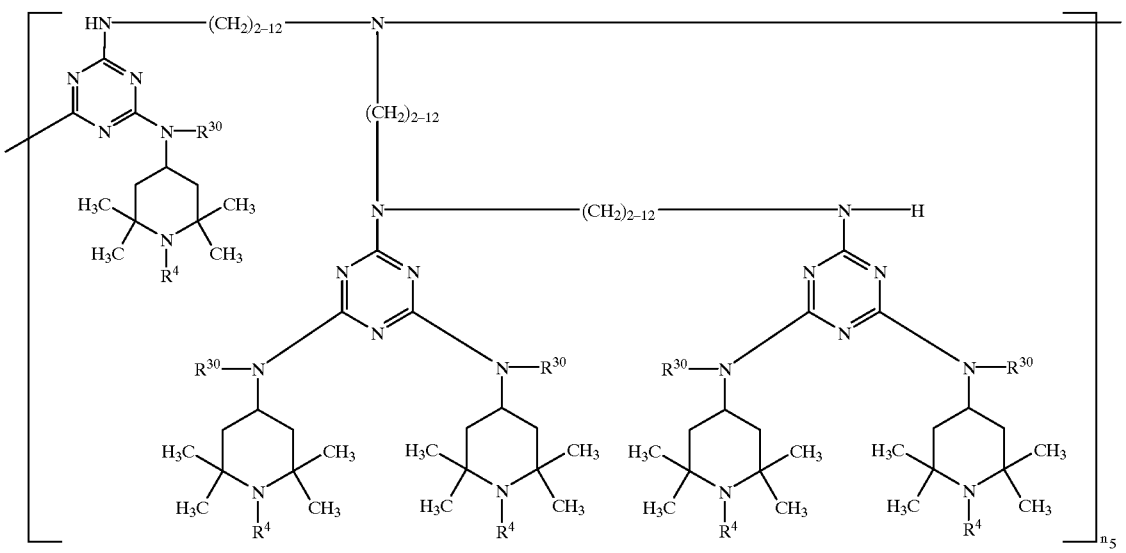

(B4-2)

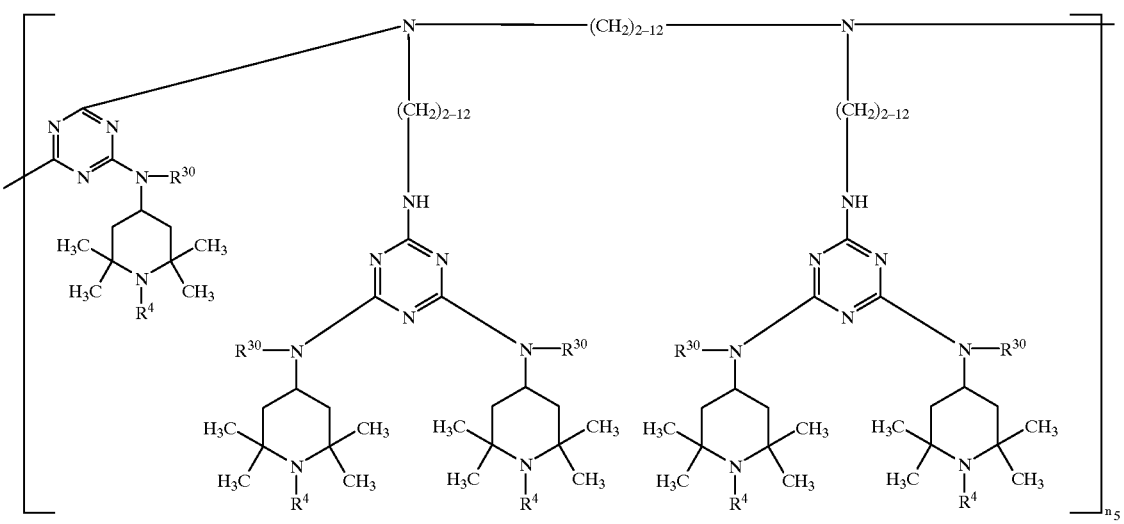

(B4-3)

or a mixture thereof, in which
$n_5$ is 1 to 20,
$R^4$ and $R^{30}$ are as defined above;

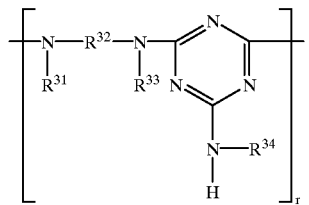

B5 where
r is as defined for formula B1,
$R^{31}$, $R^{33}$ and $R^{34}$ independently of one another are hydrogen, $C_1$–$C_{12}$-alkyl, $C_5$–$C_{12}$-cycloalkyl, $C_1$–$C_4$-alkyl-substituted $C_5$–$C_{12}$-cycloalkyl, phenyl, —OH— and/or $C_1$–$C_{10}$-alkyl-substituted phenyl, $C_7$–$C_9$-phenylalkyl, $C_7$–$C_9$-phenylalkyl substituted on the phenyl radical by —OH and/or $C_1$–$C_{10}$-alkyl, or a group of the formula B5a

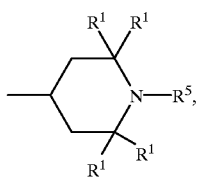

B5a where
$R^1$ and $R^5$ are as defined above, and
$R^{32}$ is $C_2$–$C_{18}$-alkylene, $C_5$–$C_7$-cycloalkylene or $C_1$–$C_4$-alkylenedi($C_5$–$C_7$-cycloalkylene) or the radicals $R^{31}$, $R^{32}$ and $R^{33}$ together with the nitrogen atoms to which they are attached, form a 5- to 10-membered heterocyclic ring, and where at least one of the radicals $R^{31}$, $R^{33}$ and $R^{34}$ is a group of the formula B5a;

B6
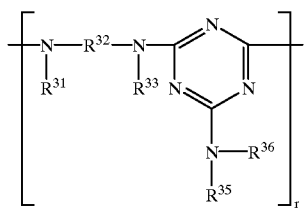

in which $R^{31}$, $R^{32}$, $R^{33}$ and r are as defined above, $R^{35}$ and $R^{36}$ independently of one another can have the definition of $R^{34}$, or $R^{35}$ and $R^{36}$, together with the nitrogen atom to which they are attached, form a 5- to 10-membered heterocyclic ring which may in addition to the nitrogen heteroatom contain one or more other heteroatoms, preferably an oxygen atom, and at least one of the radicals $R^{31}$, $R^{33}$, $R^{35}$ and/or $R^{36}$ is a group of the formula (B5a);

B7
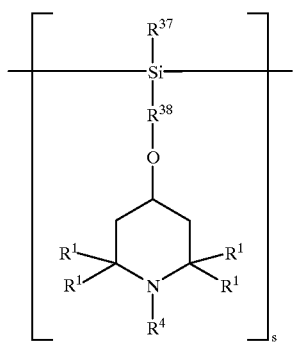

where $R^1$ and $R^4$ are as defined in claim 1, s is as defined for formula B3, $R^{37}$ is $C_1$–$C_{10}$-alkyl, $C_5$–$C_{12}$-cycloalkyl, $C_1$–$C_4$-alkyl-substituted $C_5$–$C_{12}$-cycloalkyl, phenyl or $C_1$–$C_{10}$-alkyl-substituted phenyl, and $R^{38}$ is $C_3$–$C_{10}$-alkylene.

The compounds described as components B1 to B4 are essentially known (in some cases obtainable commercially) and can be prepared by known methods as described, for example, in U.S. Pat. No. 4,233,412, U.S. Pat. No. 4,340,534, U.S. Pat. No. 4,857,595, DD-A-262 439 (Derwent 89-122 983/17, Chemical Abstracts 111:58 964u), DE-A-4 239 437 (Derwent 94-177 274/22), U.S. Pat. No. 4,529,760, U.S. Pat. No. 4,477,615 and Chemical Abstracts—CAS No. 136 504-96-6.

Component B4 can be prepared in analogy to known methods: for example, by reacting a polyamine of the formula B4a with cyanuric chloride in a molar ratio of from 1:2 to 1:4 in the presence of anhydrous lithium, sodium or potassium carbonate in an organic solvent such as 1,2-dichloroethane, toluene, xylene, benzene, dioxane or tert-amyl alcohol at a temperature of from −20° C. to +10° C., preferably from −10° C. to +10° C. and, in particular, from 0° C. to +10° C. for 2 to 8 hours and then reacting the resulting product with a 2,2,6,6-tetramethyl-4-piperidylamine of the formula B4b. The molar ratio of 2,2,6,6-tetramethyl-4-piperidylamine to polyamine of the formula B4a employed is, for example, from 4:1 to 8:1. The amount of 2,2,6,6-tetramethyl-4-piperidylamine can be added all at once or in two or more portions with an interval of several hours.

The ratio of polyamine of the formula B4a to cyanuric chloride to 2,2,6,6-tetramethyl-4-piperidylamine of the formula B4b is preferably from 1:3:5 to 1:3:6.

The following example indicates one possibility for the preparation of the preferred component B4.

Example: 23.6 g (0.128 mol) of cyanuric chloride, 7.43 g (0.0426 mol) of N,N'-bis[3-aminopropyl]ethylenediamine and 18 g (0.13 mol) of anhydrous potassium carbonate are reacted in 250 ml of 1,2-dichloroethane at 5° C. with stirring for 3 hours. The mixture is heated at room temperature for a further 4 hours. 27.2 g (0.128 mol) of N-(2,2,6,6-tetramethyl-4-piperidyl)butylamine are added and the resulting mixture is heated at 60° C. for 2 hours. A further 18 g (0.13 mol) of anhydrous potassium carbonate are added, and the mixture is heated at 60° C. for a further 6 hours. The solvent is distilled off under a gentle vacuum (200 mbar) and replaced by xylene. 18.2 g (0.085 mol) of N-(2,2,6,6-tetramethyl-4-piperidyl)butylamine and 5.2 g (0.13 mol) of ground sodium hydroxide are added, the mixture is heated to reflux for 2 hours, and the water formed in the course of the reaction is removed by azeotropic distillation for a further 12 hours. The mixture is filtered. The solution is washed with water and dried over $Na_2SO_4$. The solvent is evaporated and the residue is dried at 120–130° C. under vacuum (0.1 mbar), giving component B4 as a colorless resin.

In general component B4 can be represented, for example, by a compound of the formula B4-1, B4-2 or B4-3. It can also be present as a mixture of these three compounds.

A preferred meaning of the formula B4-1 is

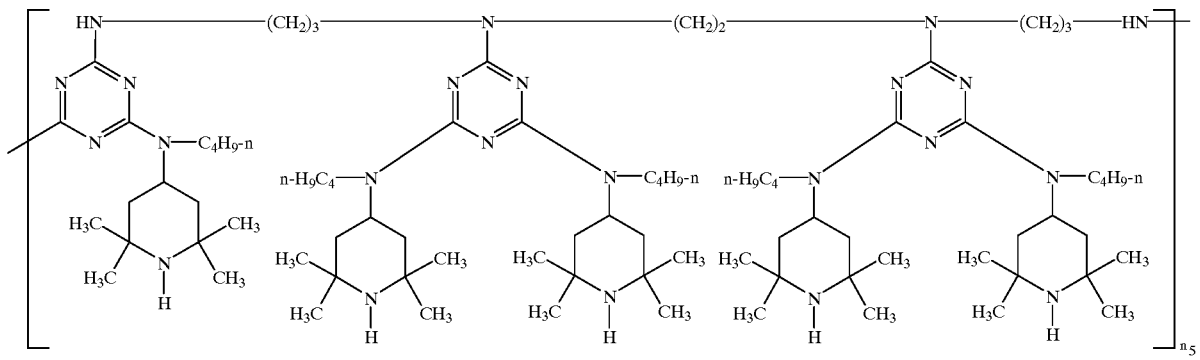

A preferred meaning of the formula B4-2 is

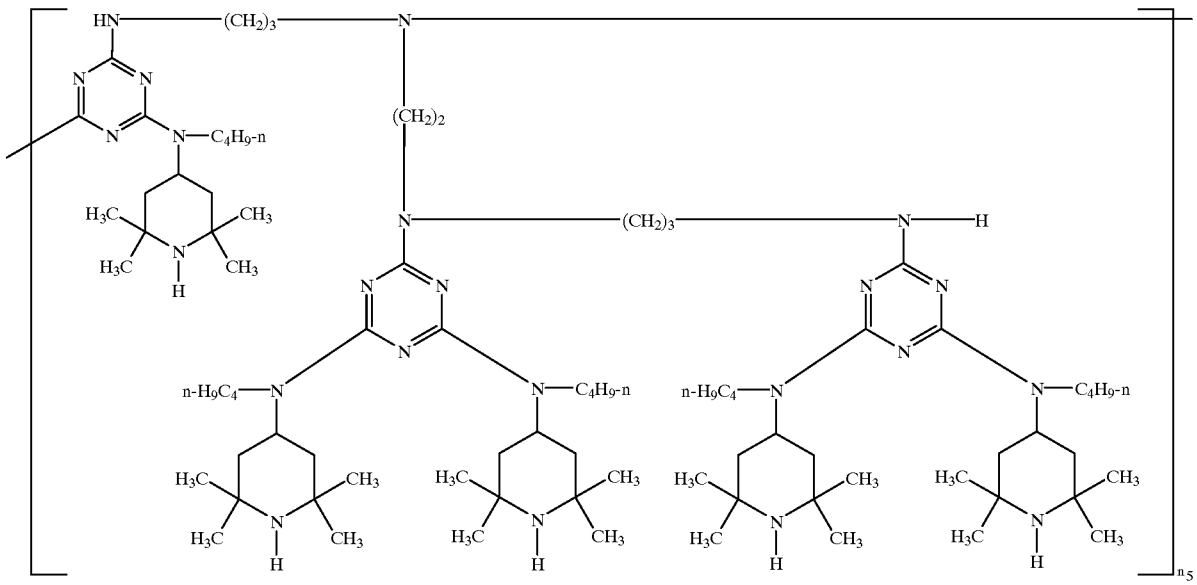

A preferred meaning of the formula B4-3 is

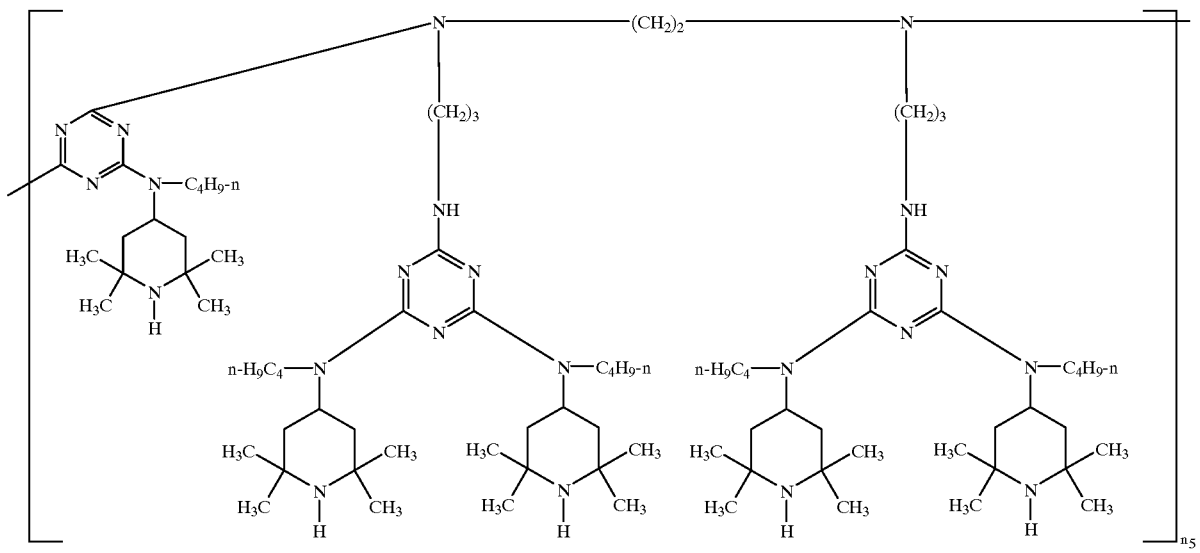

Preference is given to mixtures of compounds of the formula (III) with compounds of the formulae B1 to B7 in which n and m independently of one another are a number from 0 to 10, but n and m cannot both be 0, $R^1$ is hydrogen or a $C_1$–$C_4$-alkyl group, $R^2$ and $R^3$ independently of one another are a hydrogen atom or a $C_1$–$C_8$-alkyl group or, together with the carbon atom connecting them, are a 6- to 12-membered ring or, together with the carbon atom connecting them, are a group of the formula (IV), $R^4$ and $R^5$ independently of one another are either hydrogen or a $C_1$–$C_5$-alkyl group, an oxygen radical O*, —OH, —NO, —CH$_2$CN, benzyl, allyl, a $C_1$–$C_{10}$-alkyloxy group, a $C_5$–$C_6$-cycloalkyloxy group, a $C_6$–$C_7$-aryloxy group in which additionally the aryl radical may also be substituted, a $C_7$–$C_{10}$-arylalkyloxy group in which additionally the aryl radical may also be substituted, a $C_3$–$C_6$-alkenyl group, a $C_3$–$C_6$-alkynyl group, a $C_1$–$C_4$-acyl group, halogen, or $C_7$–$C_9$-phenylalkyl which is unsubstituted or substituted on the phenyl ring by $C_1$–$C_2$-alkyl, $R^{13}$ is hydrogen or methyl, $R^{14}$ is $C_1$–$C_5$-alkylene, $R^{17}$, $R^{21}$ are hydrogen or $C_1$–$C_4$-alkyl, $R^{15}$, $R^{18}$ are a direct bond, $R^{16}$, $R^{20}$ are $C_1$–$C_{25}$-alkyl, phenyl, $R^{19}$ is hydrogen, $C_1$–$C_{12}$-alkyl or a group of the formula B2a, $R^{25}$, $R^{26}$, $R^{27}$, $R^{28}$ and $R^{29}$ independently of one another are a direct bond or $C_1$–$C_5$-alkylene, $R^{30}$ is hydrogen, $C_1$–$C_4$-alkyl, $C_5$–$C_6$-cycloalkyl or phenyl, $R^{31}$, $R^{33}$ and $R^{34}$ independently of one another are hydrogen, $C_1$–$C_{10}$-alkyl, $C_5$–$C_6$-cycloalkyl or a group of the formula B5a, $R^{32}$ is $C_2$–$C_{10}$-alkylene, $C_5$–$C_6$-cycloalkylene, $R^{35}$ and $R^{36}$ independently of one another are as defined for $R^{34}$, or $R^{35}$ and $R^{36}$, together with the nitrogen atom to which they are attached, form a 5- to 7-membered heterocyclic ring which may also contain one or more heteroatoms, preferably an oxygen atom, and at least one of the radicals $R^{31}$, $R^{33}$, $R^{35}$ and/or $R^{36}$ is a group of the formula B5a, $R^{37}$ is $C_1$–$C_5$-alkyl, $C_5$–$C_6$-cycloalkyl or phenyl, $R^{38}$ is $C_3$–$C_5$-alkylene and $n_{5'}, n_{5''}, n_{5'''}$ are 2 to 4.

Very particularly preferred mixtures are those in which n and m independently of one another are a number from 0 to 5, but n and m cannot both be 0, $R^1$ is methyl, $R^2$ and $R^3$, together with the carbon atom connecting them, are a 12-membered ring or, together with the carbon atom connecting them, a group of the formula (IV), $R^4$ and $R^5$ independently of one another are hydrogen, acetyl, methyl, octyloxy or cyclohexyloxy, $R^{13}$ is hydrogen, $R^{14}$ is ethylene, $R^{17}$, $R^{21}$ are hydrogen or methyl, $R^{15}$ $R^{18}$ are a direct bond, $R^{16}$, $R^{20}$ are $C_1$–$C_{25}$-alkyl or phenyl, $R^{19}$ is hexadecyl or a group of the formula B2a, $R^{25}$, $R^{27}$ is methylene, $R^{26}$ is a direct bond, $R^{28}$ is 2,2-dimethylethylene, $R^{29}$ is 1,1-dimethylethylene, $R^{30}$ is n-butyl, $R^{31}$, $R^{33}$ and $R^{34}$ independently of one another are isooctyl, cyclohexyl or 2,2,6,6-tetramethylpiperid-4-yl, and at least one of the radicals $R^{31}$, $R^{33}$ and $R^{34}$ must be 2,2,6,6-tetramethylpiperid-4-yl, $R^{32}$ is hexamethylene, $R^{35}$ and $R^{36}$ independently of one another are as defined for $R^{34}$, or $R^{35}$ and $R^{36}$, together with the nitrogen atom to which they are attached, form a 6-membered heterocyclic ring which also contains an oxygen atom and so is morpholine, and at least one of the radicals $R^{31}$, $R^{33}$, $R^{35}$ and/or $R^{36}$ must be a radical 2,2,6,6-tetramethylpiperid-4-yl, $R^{37}$ is methyl, $R^{38}$ is trimethylene, $n_{5'}, n_{5''}, n_{5'''}$ are 2 to 4.

Very particular preference is given to mixtures wherein the polymeric HALS compounds in combination with compounds of the formula (III) are the following substances:

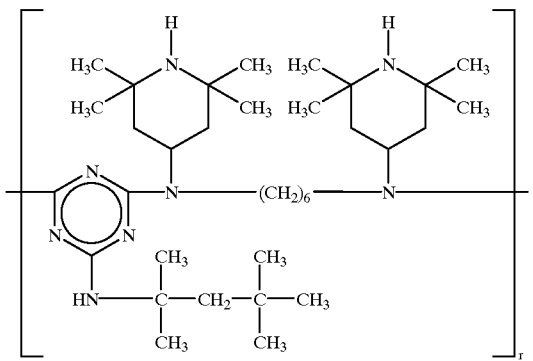

B'1

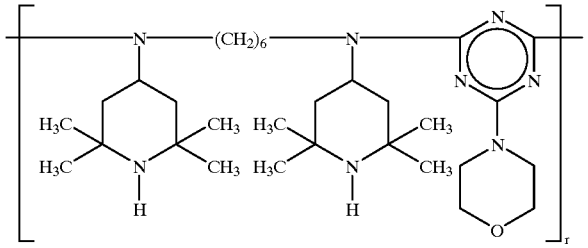

B'2

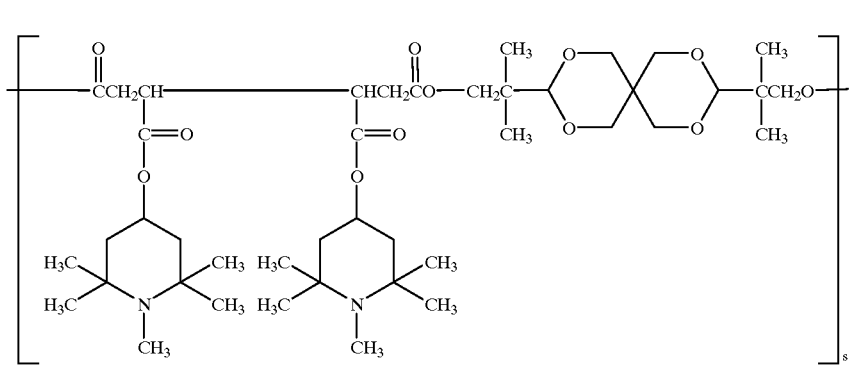
B′3
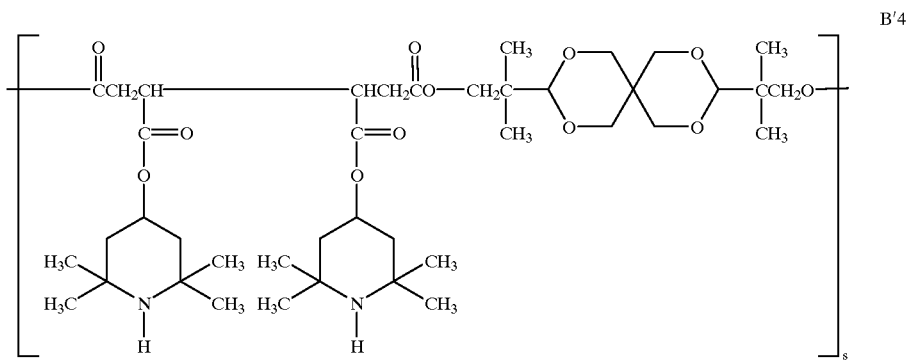
B′4
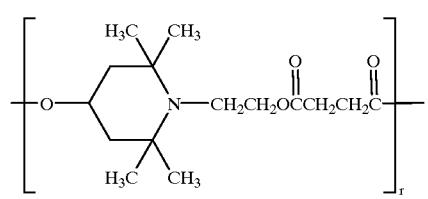
B′5
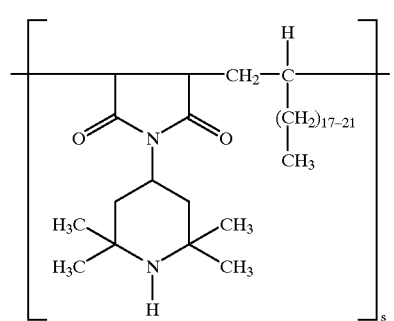
B′6
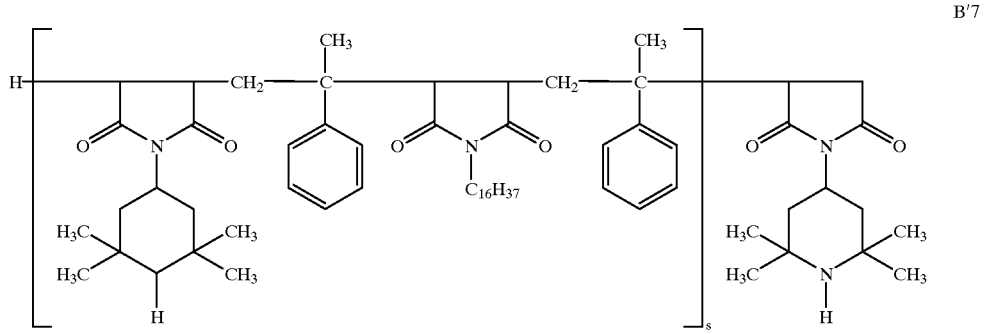
B′7

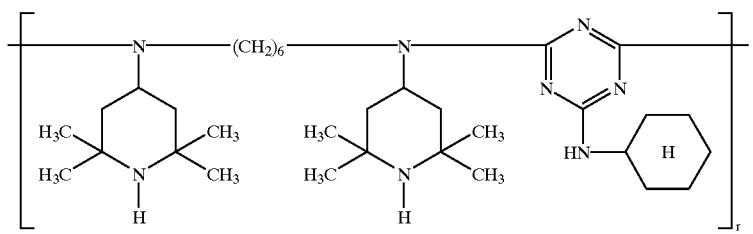
B'8
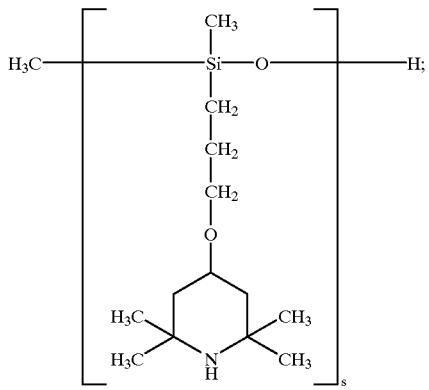
B'9
a product B'10 obtainable by reacting a polyamine of the formula B'10a:
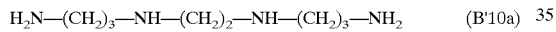 (B'10a)
with cyanuric chloride and then reacting the resulting product with a compound of the formula (B'10b)
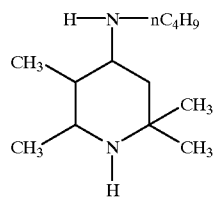 (B'10b)
where B'10 is a compound of the formula B4-1', B4-2', B4-3'
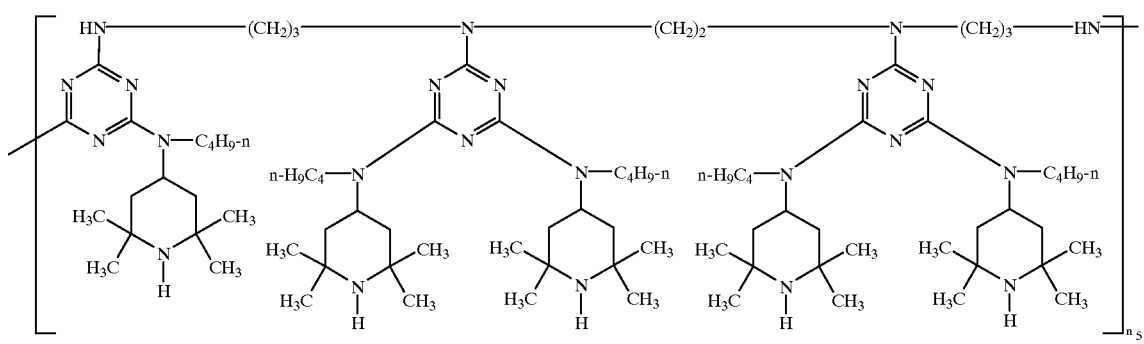
B4-1'

-continued

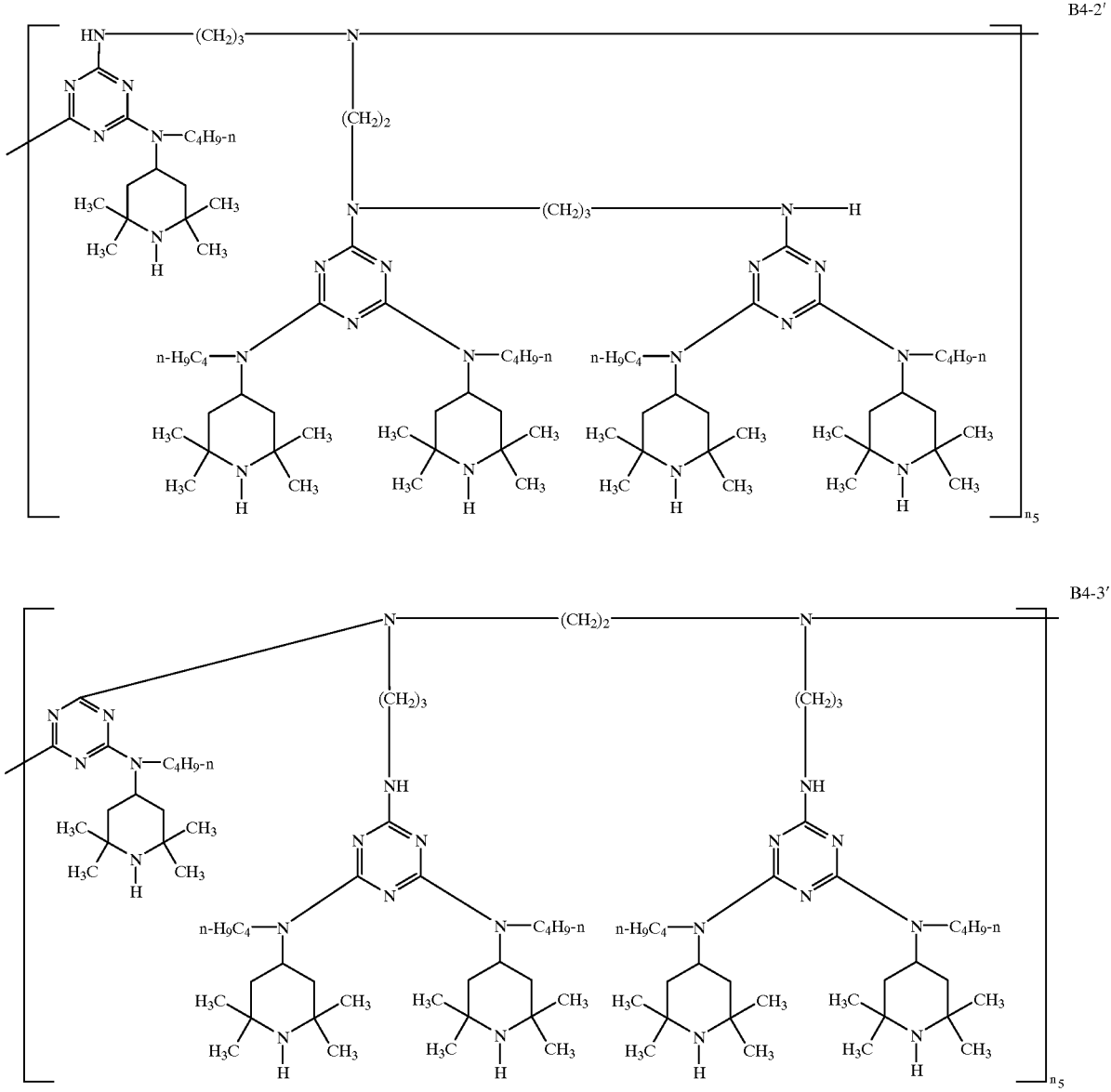

or a mixture thereof, where $n_5$ is 1 to 20.

Of the mixtures described above, particular preference is given to those in which the other co-component(s) is(are) CHIMASSORB® 944, TINUVIN® 622, DASTIB® 1082, UVASORB® HA 88, UVINUL® 5050, LOWILITE® 62, UVASIL® 299, CYASORB® 3346, MARK LA 63®, MARK® LA 68 or LUCHEM® B 18.

Surprisingly, it was found that the simultaneous use of the new compounds (III) and of the monomeric or polymeric HALS stabilizers described above gives rise to marked synergistic effects.

Also of particular advantage is the combination of compound (III) with phosphites, in the sense that the stabilizer (III) suppresses or reduces the hydrolytic breakdown of the phosphite, as in EP-A-400454, EP-A-592364, EP-A-143464, EP-A-576833, EP-A-558040, EP-A-278578, EP-A-676405, DE-A-4418080. Compound (III) is particularly suitable for stabilizing phosphites of the formulae C1 to C7:

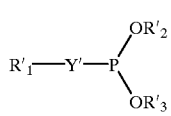
C1

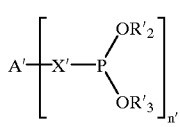
C2

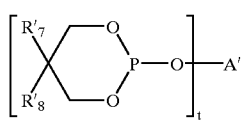
C3

-continued

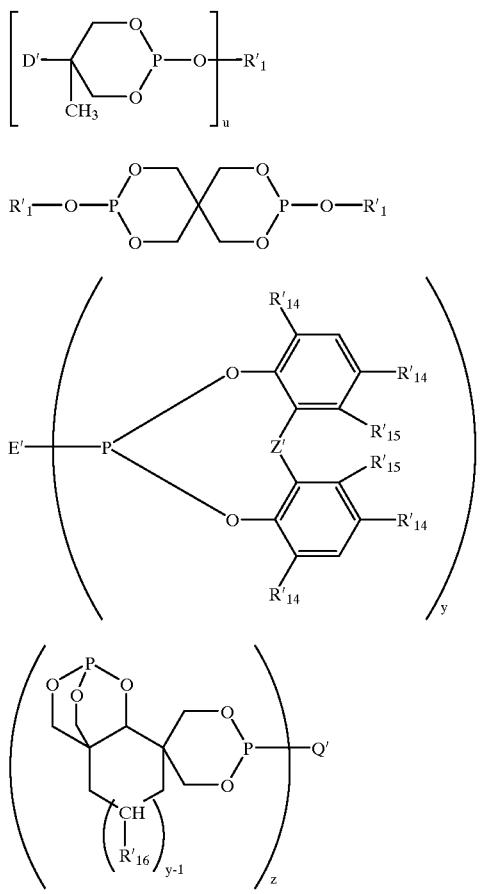

C4

C5

C6

C7

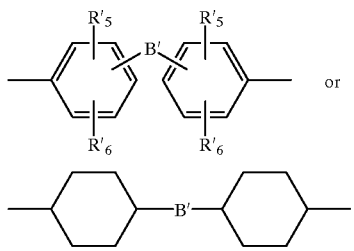

in which the indices are integral and
n' is 2,3 or 4; u is 1 or 2; t is 2 or 3; y is 1, 2 or 3; and z is 1 to 6; A', if n' is 2, is alkylene of 2 to 18 carbon atoms, —S—, —O— or —NR'$_4$-interrupted alkylene of 2 to 12 carbon atoms; a radical of one of the formulae

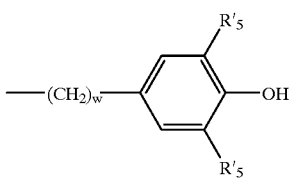

or phenylene;
A', if n' is 3, is a radical of the formula —C$_r$H$_{2r-1}$;
A', if n' is 4, is the radical of the formula

A" is as defined for A' if n' is 2;
B' is a radical of the formula —CH$_2$—; —CHR'$_4$—; —CR'$_1$R'$_4$—; —S— or a direct bond;
or is C$_5$–C$_7$-cycloalkylidene; or is cyclohexylidene substituted in position 3, 4 and/or 5 by 1 to 4 C$_1$–C$_4$-alkyl radicals,
D', if u is 1, is methyl and, if u is 2, is —CH$_2$OCH$_2$—;

E', if y is 1, is alkyl of 1 to 18 carbon atoms, phenyl, a radical of the formula —OR'$_1$ or halogen;
E', if y is 2, is a radical of the formula O—A"—O—;
E', if y is 3, is a radical of the formula

or N(CH$_2$—CH$_2$—O—)$_3$;
Q' is the radical of an at least z-valent alcohol or phenol which is attached to the phosphorus atom(s) via the alcoholic and/or phenolic oxygen atom(s);
R'$_1$, R'$_2$ and R'$_3$ independently of one another are alkyl of 1 to 30 carbon atoms; halogen-, —COOR'$_4$—, —CN— or —CONR'$_4$R'$_4$-substituted alkyl of 1 to 18 carbon atoms; —S—, —O— or —NR'$_4$-interrupted alkyl of 2 to 18 carbon atoms; phenyl-C$_1$–C$_4$-alkyl; cycloalkyl of 5 to 12 carbon atoms; phenyl or naphthyl; phenyl or naphthyl substituted by halogen, 1 to 3 alkyl radicals or alkoxy radicals having in total 1 to 18 carbon atoms or phenyl-C$_1$–C$_4$-alkyl; or a radical of the formula in which w is an integer from the range 3 to 6;
R'$_4$ or the radicals R'$_4$ independently of one another is or are hydrogen, alkyl of 1 to 18 carbon atoms, cycloalkyl of 5 to 12 carbon atoms, or phenylalkyl of 1 to 4 carbon atoms in the alkyl moiety;
R'$_5$ and R'$_6$ independently of one another are hydrogen, alkyl of 1 to 8 carbon atoms or cycloalkyl of 5 or 6 carbon atoms;
R'$_7$ and R'$_8$, if t=2, independently of one another are C$_1$–C$_4$-alkyl or together are a 2,3-dehydropentamethylene radical; and
R'$_7$ and R'$_8$, if t=3, are methyl;
the substituents R'$_{14}$ independently of one another are hydrogen, alkyl of 1 to 9 carbon atoms or cyclohexyl;
the substituents R'$_{15}$ independently of one another are hydrogen or methyl; and
R'$_{16}$ is hydrogen or C$_1$–C$_4$-alkyl and, if two or more radicals R'$_{16}$ are present, the radicals R'$_{16}$ are identical or different;
X' and Y' are each a direct bond or —O—; and
Z is a direct bond; —CH$_2$—; —C(R'$_{16}$)$_2$— or —S—.
Particularly preferred phosphites or phosphonites of the formulae C1, C2, C5 or C6 are those in which
n' is the number 2 and y is the number 1 or 2;
A' is alkylene of 2 to 18 carbon atoms; p-phenylene or p-biphenylene;
E', if y=1, is C$_1$–C$_{18}$-alkyl, —OR$_1$ or fluorine; and, if y=2, is p-biphenylene;
R'$_1$, R'$_2$ and R'$_3$ independently of one another are alkyl of 1 to 18 carbon atoms; phenyl-C$_1$–C$_4$-alkyl; cyclohexyl; phenyl; or phenyl substituted by 1 to 3 alkyl radicals having in total 1 to 18 carbon atoms;
the substituents R'$_{14}$ independently of one another are hydrogen or alkyl of 1 to 9 carbon atoms;

$R'_{15}$ is hydrogen or methyl;
X' is a direct bond;
Y' is —O—; and
Z' is a direct bond or —CH($R'_{16}$)—.

Very particularly preferred phosphites or phosphonites of one of the formulae C1, C2, C5 or C6 are those in which
n' is the number 2 and y is the number 1;
A' is p-biphenylene;
E' is $C_1$–$C_{18}$-alkoxy;

$R'_1$, $R'_2$ and $R'_3$ independently of one another are phenyl substituted by 2 or 3 alkyl radicals having in total 2 to 12 carbon atoms;
the substituents $R'_{14}$ independently of one another are methyl or tert-butyl;
$R'_{15}$ is hydrogen;
X' is a direct bond;
Y' is —O—; and
Z' is a direct bond, —CH$_2$— or —CH(CH$_3$)—.

Special mention should be made of the specific phosphorus compounds of the formulae C'1 to C'12:

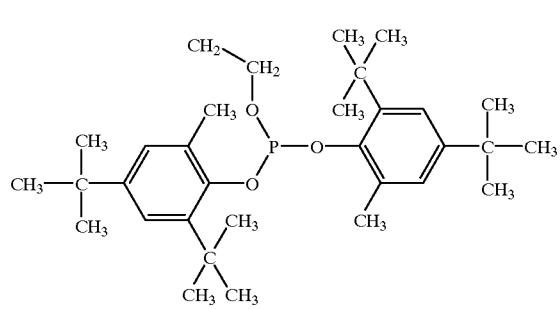

C'1

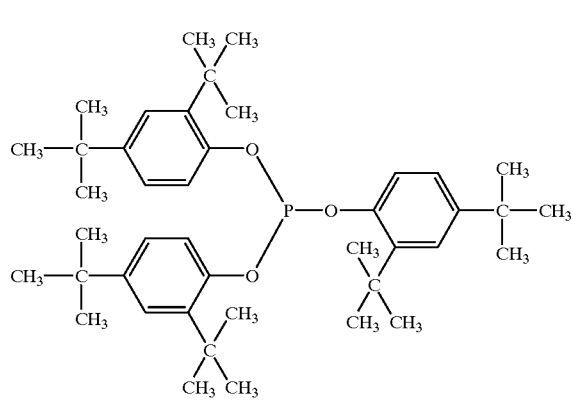

C'2

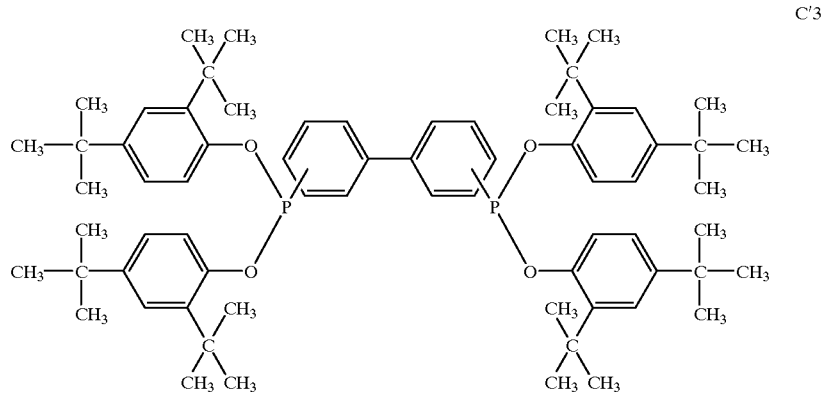

C'3

In the formula C'3, the two substituents of phosphorus are located primarily in positions 4 and 4' of the biphenyl parent structure
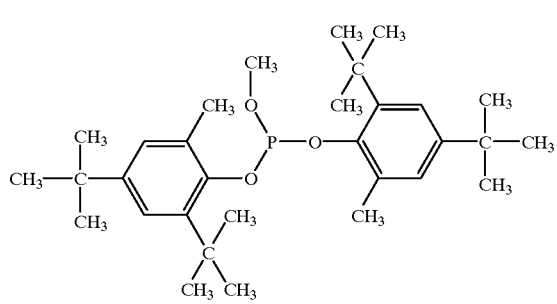
C'4
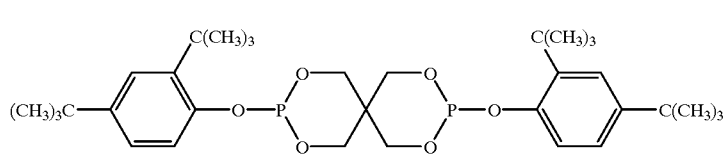
C'5
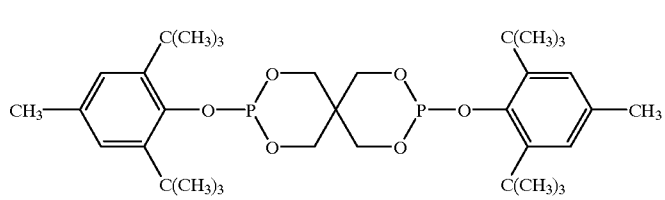
C'6
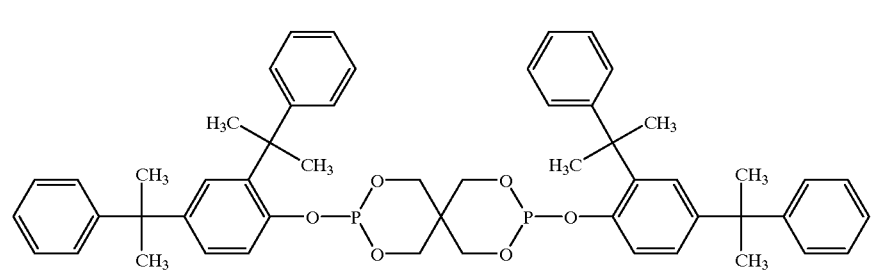
C'7
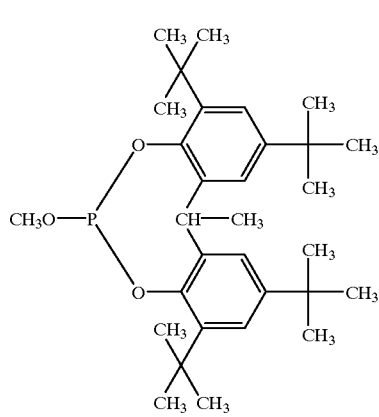
C'8

-continued

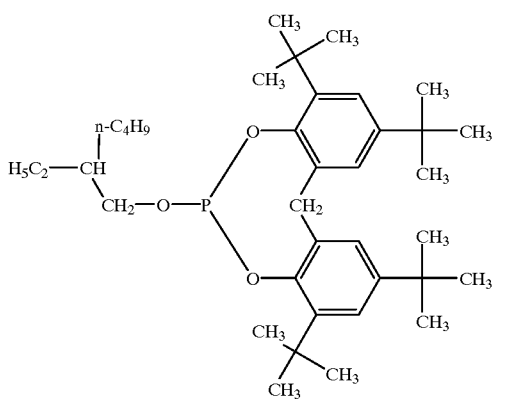

C'9

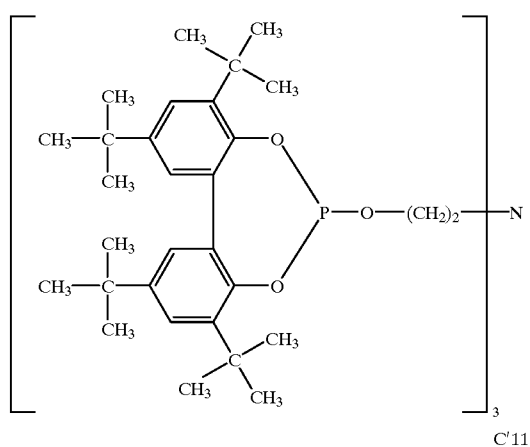

C'10

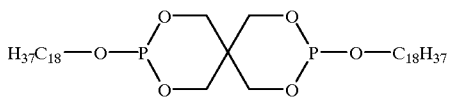

C'11

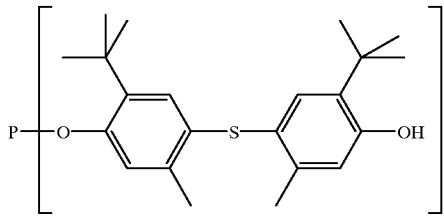

C'12

The phosphites and phosphonites mentioned are known compounds, and in some cases are obtainable commercially.

The following stabilizer mixtures comprise particularly suitable embodiments of the invention:

Compound III and IRGAFOS® 38,
Compound III and IRGAFOS® 12,
Compound III and HOSTANOX® PAR 24,
Compound III and HOSTANOX® OSP 1,
Compound III and IRGAFOS® P-EPQ™,
Compound III and ULTRANOX® 626,
Compound III and ULTRANOX® 618,
Compound III and MARK® PEP-36 (from Asahi Denka),
Compound III and MARK® HP10 (from Asahi Denka),
Compound III and DOVERPHOS® 9228.

The combination of compound (III) with phosphites is also outstandingly suitable in the sense that the phosphite synergistically supports the action of the compound (III) in connection with the stabilization of organic material. Synergistic effects of this kind are described in EP-A-359276 und EP-A-567117. Mixtures of the compound (III) with phosphites of the formulae C'1 to C'12 are particularly suitable.

The compound (III) is also outstandingly suitable for combination with phosphite and/or with a sterically hindered phenol and/or with an acid scavenger. It is particularly appropriate to combine the compound (III) in mixtures with phosphite, phenol and acid scavenger in a manner as described in DE-A-19537140.

The compound (III) and the mixtures described above are also suitable for synergistic combination with other light stabilizers, such as those, for example, from the class of the UV absorbers (2-hydroxybenzophenones or 2-hydroxyphenylbenzotriazoles, cinnamic acid derivatives, oxanilides) and/or nickel quenchers.

In the mixtures described above, the proportion of compounds of the formula (III) can be between 1 and 99% by weight.

The compound (III) is also suitable for use in combination with zeolites or hydrotalcites, such as ®DHT4A, in analogy to EP-A-429731.

The compound (III) and the mixtures described above can also be combined with one or more N,N-dialkyl-substituted hydroxylamines, preferably with N,N-dioctadecylhydroxylamine.

Furthermore, the compound (III) can be combined with one or more basic or other acid-binding costabilizers from the group consisting of the metal carboxylates, oxides, hydroxides and carbonates, and/or zeolites, and/or hydrotalcites.

Preferred costabilizers are calcium stearate, and/or magnesium stearate, and/or magnesium oxide, and/or zinc oxide, and/or carbonate-containing zinc oxide and/or hydrotalcites.

Particularly preferred costabilizers are ZINKOXID® AKTIV, ZINKOXID® TRANSPARENT and/or one of the hydrotalcites DHT® 4A, DHT4® A2, KYOWAAD® 200, KYOWAAD® 300, KYOWAAD® 400, KYOWAAD® 500, KYOWAAD® 600, KYOWAAD® 700, KYOWAAD® 1000, and KYOWAAD® 2000.

The compound (III) is highly suitable for stabilizing pigments, alone or in appropriate combination with one or more further stabilizers, as in EP-A-241419, EP-A-612792, EP-A-612816, or for stabilizing leather, as in EP-A-665294 and DE-A-4411369.

The result of these new combinations are mixtures having an improved profile of properties with respect to the individual components; for example, having synergies in the photoprotective effect. Combinations of light stabilizers with acid scavengers are described in U.S. Pat. No. 5,134,181, U.S. Pat. No. 4,929,652, U.S. Pat No. 5,037,870, U.S. Pat No. 5,180,762.

Other compounds which lend themselves to advantageous combination with the compounds of the formula (III) or with the above-described mixtures are
synergists of the 3-pyrazolidinone type
synergists of the 3-arylbenzofuran-2-one type
dyes or pigments based on organic or inorganic substances.

Of the 3-arylbenzofuran-2-ones, preference is given to 3-(3,4-dimethylphenyl)-5,7-di-tert-butyl-3H-benzofuran-2-one (formula D)

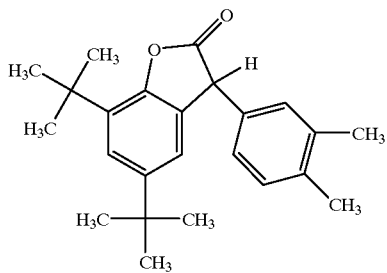

Combinations with synergists of the 3-pyrazolidinone type and 1,2,4-triazolidine-3,5-dione type are described in EP-A-517658.

This combination is particularly suitable for applications in organic material, preferably in polymeric material, especially films, fibers and tapes and/or fabric produced therefrom, which are in contact with aggressive chemicals, especially with crop protection products. Combinations of this kind are described in EP-A-690094.

The present invention additionally provides an organic material stabilized against the effect of light, oxygen and heat, especially a plastic, coating material, lacquer or oil comprising compounds of the formula (III) in the concentrations indicated above.

Examples of such materials are:
1. Polymers of monoolefins and diolefins, for example polypropylene, polyisobutylene, polybut-1-ene, poly-4-methylpent-1-ene, polyisoprene or polybutadiene, as well as polymers of cycloolefins, for example of cyclopentene or norbornene; furthermore polyethylene (which optionally can be crosslinked); for example, high density polyethylene (HDPE), polyethylene of high density and high molar mass (HDPE-HMW), polyethylene of high density and ultrahigh molar mass (HDPE-UHMW), medium density polyethylene (HMDPE), low density polyethylene (LDPE), linear low density polyethylene (LLDPE), branched low density polyethylene (BLDPE).

Polyolefins, i.e. polymers of monoolefins exemplified in the preceding paragraph, in particular polyethylene and polypropylene, can be prepared by various, and especially by the following, methods:
a) free-radical polymerization (normally under high pressure and at elevated temperature)
b) catalytic polymerization using a catalyst that normally contains one or more metals of group IVb, Vb, VIb or VIII of the Periodic Table. These metals usually have one or more ligands, such as oxides, halides, alcoholates, esters, ethers, amines, alkyls, alkenyls and/or aryls that may be either π- or σ-coordinated. These metal complexes may be in the free form or fixed on substrates, for example on activated magnesium chloride, titanium(III) chloride, alumina or silicon oxide. These catalysts may be soluble or insoluble in the polymerization medium. The catalysts can be active as such in the polymerization or further activators may be used, for example metal alkyls, metal hydrides, metal alkyl halides, metal alkyl oxides or metal alkyloxanes, the metals being elements of groups Ia, IIa and/or IIIa of the Periodic Table. The activators may be modified, for example, with further ester, ether, amine or silyl ether groups. These catalyst systems are usually termed Phillips, Standard Oil Indiana, Ziegler (-Natta), TNZ (DuPont), metallocene or single site catalysts (SSC).
2. Mixtures of the polymers mentioned under 1), for example mixtures of polypropylene with polyisobutylene, polyethylene with polyisobutylene, polypropylene with polyethylene (for example PP/HDPE/LDPE) and mixtures of different types of polyethylene (for example LDPE/HDPE) with one another.
3. Copolymers of monoolefins and diolefins with each other or with other vinyl monomers, for example ethylene-propylene copolymers, linear low density polyethylene (LLDPE) and mixtures thereof with low density polyethylene (LDPE), propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide or ethylene-acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned under 1), for example polypropylene-ethylene-propylene copolymers, LDPE-ethylene-vinyl acetate copolymers, LDPE-ethylene-acrylic acid copolymers, LLDPE-ethylene-vinyl acetate copolymers, LLDPE-ethylene-acrylic acid copolymers and alternating or random polyalkylene-carbon monoxide copolymers and mixtures thereof with other polymers, for example polyamides.

4. Hydrocarbon resins (for example $C_5$–$C_9$) including hydrogenated modifications thereof (e.g. tackifier resins) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methacrylate; mixtures of high impact strength of styrene copolymers and another polymer, for example a polyacrylate, a diene polymer or an ethylene-propylene-diene terpolymer; and block copolymers of styrene, such as styrene-butadiene-styrene, styrene-isoprene-styrene, styrene-ethylene/butylene-styrene or styrene-ethylene/propylene-styrene.

7. Graft copolymers of styrene or α-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, as well as mixtures thereof with the copolymers mentioned under 6), for example the copolymer mixtures known as ABS, MBS, ASA or AES polymers.

8. Halogen-containing polymers, such as polychloroprene, chlorinated rubber, chlorinated and brominated copolymer of isobutylene-isoprene (halobutyl ruuber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride; as well as copolymers thereof such as vinyl chloride-vinylidene chloride, vinyl chloride-vinyl acetate or vinylidene chloride-vinyl acetate.

9. Polymers derived from α,β-unsaturated acids and derivatives thereof, such as polyacrylates and polymethacrylates, polyacrylonitriles, polyacrylamides and polymethyl methacrylates impact-modified with butyl acrylate.

10. Copolymers of the monomers mentioned under 9) with each other or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

11. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in section 1.

12. Homopolymers and copolymers of cyclic ethers, such as polyalkylene glycols, polyethylene oxide, polypropylene oxide or copolymers thereof with bisglycidyl ethers.

13. Polyacetals such as polyoxymethylene and those polyoxymethylenes which contain comonomers, for example ethylene oxide; polyacetals modified with thermoplastic polyurethanes, acrylates or MBS.

14. Polyphenylene oxides and sulfides, and mixtures thereof with styrene polymers or polyamides.

15. Polyurethanes derived from hydroxyl-terminated polyethers, polyesters and polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, such as polyamide 4, 6, 6/6, 6/10, 6/9, 6/12, 4/6, 12/12, 11 and 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol. As well as polyamides or copolyamides modified with EPDM or ABS; and polyamides condensed during processing (RIM polyamide systems).

17. Polyureas, polyimides, polyamide-imides, polyether imides, polyester amides, polyhydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, as well as block polyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example from epoxy acrylates, urethane acrylates or polyester acrylates.

25. Alkyd resins, polyester resins and acrylic resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, examples being products of bisphenol A diglycidyl ethers, bisphenol F diglycidyl ethers, which are crosslinked by means of customary hardeners, such as anhydrides or amines, for example, with or without accelerators.

27. Natural polymers such as cellulose, natural rubber, gelatin and derivatives thereof which have been chemically modified in a polymer-homologous manner, for example cellulose acetates, cellulose propionates and cellulose butyrates, or the cellulose ethers such as methyl cellulose; as well as rosins and derivatives.

28. Mixtures (polyblends) of the aforementioned polymers, for example PP/EPDM, polyamide/EPDM or ABS, PVC/EVA, PVC/ABS, PVC/MBS, PC/ABS, PBT/ABS, PC/ASA, PC/PBT, PVC/CPE, PVC/acrylates, POM/thermoplastic PUR, PC/thermoplastic PUR, POM/acrylate, POM/MBS, PPO/MBS, PPO/HIPS, PPO/PA 6.6 and copolymers, PA/HDPE, PA/PP, PA/PPO, PBT/ABS or PBT/PET/PC.

29. Natural and synthetic organic substances which constitute pure monomeric compounds or mixtures thereof, examples being mineral oils, animal or vegetable fats, oils and waxes, or oils, waxes and fats based on synthetic esters (e.g. phthalates, adipates, phosphates or trimellitates), and also blends of synthetic esters with mineral oils in any desired proportion by weight, as are employed, for example, as spin finishes, and aqueous emulsions thereof.

30. Aqueous emulsions of natural or synthetic rubbers, such as natural rubber latex or latices of carboxylated styrene-butadiene copolymers.

The organic material stabilized by the compounds of the formula (III) of the invention or by an appropriate combination comprising this compound may if desired also comprise further additives, examples being antioxidants, light stabilizers, metal deactivators, antistatic agents, flame retardants, lubricants, nucleating agents, acid scavengers (basic costabilizers), pigments and fillers. Antioxidants and light stabilizers which are added in addition to the compounds or combinations of the invention are, for example, compounds based on sterically hindered amines or on sterically hindered phenols, or sulfur- or phosphorus-containing costabilizers. Examples of suitable additives which can additionally be employed in combination are compounds as set out below:

1. Antioxidants 1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear or sidechain-branched nonylphenols, such as 2,6-di-nonyl-4-methylphenol, 2,4-dimethyl-6-(1-methylundec-1'-yl)-phenol, 2,4-dimethyl-6-(1'-methylheptadec-1'-yl)-phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.5 Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl)butane, 2,2-bis(3,5-di-tert-butyl-4-hydroxyphenyl) propane, 2,2-bis(5-tert-bulyl-4-hydroxy-2-methylphenyl)-4-n-dodecylmercaptobutane, 1,1,5,5-tetra-(5-tert-butyl-4-hydroxy-2-methylphenyl)pentane, ethylene glycol bis[3,3-bis(3'-tert-butyl-4'-hydroxyphenyl)butyrate].

1.6. O—, N— and S-benzyl compounds, for example 3,5,3',5'-tetra-tert-butyl-4,4'-dihydroxydibenzyl ether, octadecyl 4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide, isooctyl 3,5-di-tert-butyl-4-hydroxybenzylmercaptoacetate, tridecyl 4-hydroxy-3,5-di-tert-butylbenzylmercaptoacetate.

1.7. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl) malonate, didodecyl mercaptoethyl-2,2-bis(3,5-di-tert-butyl-4-hydroxybenzyl)malonate, di-[4-(1,1,3,3-tetramethylbutyl)phenyl] 2,2-bis(3,5-di-tert-butyl-4-hydroxybenzyl)malonate.

1.8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hyd roxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurat, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

1.10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the Ca salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl) propionic acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl) propionic acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(3,5-dicyclohexyl-4-hydroxyphenyl) propionic acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenylacetic acid with mono- or polyhydric alcohols, e.g. with methanol, ethanol, n-octanol, isooctanol, octadecanol, 1,6-hexanediol, 1,9-nonanecliol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,3-bis(3'tert-butyl-4'-hydroxyphenyl)butyric acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.17. Amides of β-(3,5-di-tert-butyl-4-hydroxyphenyl) propionic acid, e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

1.18. Tocopherol, such as α-tocopherol, β-tocopherol, γ-tocopherol, δ-tocopherol and mixtures thereof (vitamin E).

1.19. Ascorbic acid (vitamin C).

1.20. Amine antioxidants, for example N,N'-diisopropyl-p-phenylenediamine, N,N'di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di(naphthyl-2-)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(-toluenesulfonamido)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, e.g. p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, di(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di-[(2-methylphenyl)amino]ethane, 1,2-di-(phenylamino)propane, (o-tolyl)biguanide, di[4-(1',3'-dimethylbutyl)phenyl]amine, tert-octylated N-phenyl-1-naphthylamine, mixture of mono- and dialkylated tert-butyl/tert-octyldiphenylamines, mixture of mono- and dialkylated nonyidiphenylamines, mixture of mono- and dialkylated dodecyidiphenylamines, mixture of mono- and dialkylated isopropyl/isohexyl-diphenylamines, mixture of mono- and dialkylated tert-butyidiphenylamines, 2,3-dihydro-3,3-dimethyl-4H-1,4-benzothiazine, phenothiazine, mixture of mono- and dialkylated tert-butyl/tert-octyl-phenothiazines, mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, bis(2,2,6,6-ietramethylpiperidin-4-yl) sebacate, 2,2,6,6-tetramethylpiperidin-4-one, 2,2,6,6-tetramethylpiperidin-4-ol.

2. UV Absorbers and Light Stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-[2'-hydroxy-5'-(1,1,3,3-tetramethylbutyl)phenyl]benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, a mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tertbutyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$ where R=3'-tert-butyl-4'-hydroxy-5'-2H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxycinnamate or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidin-4-yl) sebacate, bis(2,2,6,6-tetramethylpiperidin-4-yl) glutarate, bis(2,2,6,6-tetramethylpiperidin-4-yl) succinate, bis( 1,2,2,6,6-pentamethylpiperidin-4-yl) sebacate, bis(1,2,2,6,6-pentamethylpiperidin-4-yl) glutarate, 2,2,6,6-tetramethylpiperidyl behenate, 1,2,2,6,6-pentamethylpiperidyl behenate, the condensate of 1-hydroxyethyl-2,2,6,6-tetramethyl-4-hydroxypiperidine and succinic acid, the condensate of N,N'-bis-(2,2,6,6-tetramethyl-4-piperidyl)hexamethylendiamine and 4-tert-octylamino-2,6-dichloro-1,3,5-s-triazine, tris-(2,2,6,6-tetramethyl-4-piperidyl) nitrilotriacetate, tetrakis(2,2,6,6-tetramethyl-4-piperidyl) 1,2,3,4-butantetraoate, 1,1'-(1,2-ethanediyl)-bis-(3,3,5,5-tetramethylpiperazinone), 4-benzoyl-2,2,6,6-tetramethylpiperidine, 4-staryloxy-2,2,6,6-tetramethylpiperidine, 4-stearoyloxy-2,2,6,6-tetramethylpiperidine, 4-stearyloxy-1,2,2,6,6-pentamethylpiperidine, 4-stearoyloxy-1,2,2,6,6-pentamethylpiperidine, bis(1,2,2,6,6-pentamethylpiperidyl) 2-n-butyl-2-(2-hydroxy-3,5-di-tert-butylbenzyl)malonate, bis(1,2,2,6,6-pentamethylpiperidyl) 2-n-butyl-2-(4-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2, 2,6,6-tetramethylpiperidyl) sebacate, bis-(1-octyloxy-2,2, 6,6-tetramethylpiperidyl) succinate, the condensate of N,N'-bis(2,2,6,6-tetramethyl-4-piperidyl) hexamethylenediamine and 4-morpholino-2,6-dichloro-1, 3,5-triazine, the condensate of N,N'-bis(2,2,6,6-tetramethyl-4-piperidyl)hexamethylenediamine and 4-cyclohexylamino-2,6-dichloro-1,3,5-triazine, the condensate of 2-chloro-4,6-di-(4-n-butylamino-2,2,6,6-tetramethylpiperidyl)-1,3,5-triazine and 1,2-bis-(3-aminopropylamino)ethane, the condensate of 2-chloro-4, 6-di-(4-methoxypropylamino-2,2,6,6-tetramethylpiperidyl)-1,3,5-triazine and 1,2-bis-(3-aminopropylamino)ethane, the condensate of 2-chloro-4, 6-di-(4-methoxypropylamino-1,2,2,6,6-pentamethylpiperidyl)-1,3,5-triazine and 1,2-bis-(3-aminopropylamino)ethane, the condensate of 2-chloro-4, 6-di-(4-n-butylamino-1,2,2,6,6-pentamethylpiperidyl)-1, 3,5-triazine and 1,2-bis-(3-aminopropylamino)ethane, reaction products of 2-chloro-4,6-di-(4-n-butylamino-2,2, 6,6-tetramethylpiperidyl)-1,3,5-triazine with mono- or polyfunctional amines, where between one and all the active hydrogen atoms on the amine are replaced, such as with ethylenediamine, diethylenetriamine, triethylenetetramine, hexamethylenediamine, 1,2-bis-(3-aminopropylamino)ethane, reaction products of 2-chloro-4,6-di-( 4-n-butylamino-1,2,2,6,6-pentamethylpiperidyl)-1,3,5-triazine with mono- or polyfunctional amines, where between one and all the active hydrogen atoms on the amine are replaced, such as with ethylenediamine, diethylenetriamine, triethylenetetramin, hexamethylenediamine, 1,2-bis(3-aminopropylamino) ethane, reaction products of 2-chloro-4,6-di-(4-n-butylamino-2,2,6,6-tetramethylpiperidyl)-1,3,5-triazine and 4-tert-octylamino-2,6-dichloro-1,3,5-s-triazine with mono- or polyfunctional amines, where between one and all the active hydrogen atoms on the amine are replaced, such as with ethylenediamine, diethylenetriamine, triethylenetetramine, hexamethylenediamine, 1,2-bis(3-aminopropylamino)ethane, reaction products of 2-chloro-4,6-di-(4-n-butylamino-1,2,2,6,6-pentamethylpiperidyl)-1,3,5-triazine and 4-tert-octylamino-2,6-dichloro-1,3,5-s-triazine with mono- or polyfunctional amines, where between one and all the active hydrogen atoms on the amine are replaced, such as with ethylenediamine, diethylenetriamine, triethylenetetramine, hexamethylenediamine, 1,2-bis-(3-aminopropyl-amino) ethane, reaction products of 2-chloro-4,6-di-(4-n-butylamino-2,2,6,6-tetramethylpiperidyl)-1,3,5-triazine and 4-(4-n-butylamino-2,2,6,6-tetramethylpiperidyl)-2,6-dichloro-1,3,5-s-triazine with mono- or polyfunctional amines, where between one and all the active hydrogen atoms on the amine are replaced, such as with ethylenediamine, diethylenetriamine, triethylenetetramine, hexamethylenediamine, 1,2-bis-(3-aminopropylamino)ethane, reaction products of 2-chloro-4,6-di-(4-n-butylamino-1,2,2,6,6-pentamethylpiperidyl)-1,3,5-triazine and 4-(4-n-butylamino-2,2,6,6-tetramethylpiperidyl)-2,6-dichloro-1,3,5-s-triazine with mono- or polyfunctional amines, where between one and all the active hydrogen atoms on the amine are replaced, such as with ethylenediamine, diethylenetriamine, triethylenetetramine, hexamethylenediamine, 1,2-bis-(3-aminopropylamino)ethane, the condensate of 1,2-bis(3-aminopropylamino)ethane and 2,4,6-trichloro-1,3,5-triazine and also 4-butylamino-2,2,6,6-tetramethylpiperidine, N-(2,2,6,6-tetramethyl-4-piperidyl)-n-dodecylsuccinimide, N-(1,2,2,6,6- pentamethyl-4-piperidyl)-n-dodecylsuccinimide, 8-acetyl-3-dodecyl-7,7,9,9-tetramethyl-1,3,8-triazaspiro[4.5]decane-2,4-dione, oligomerized 2,2,4,4-tetramethyl-20-(oxiranylmethyl)-7-oxa-3,20-diaza-dispiro[5.1.11.2]heneicosan-21-one, oligomerized 1,2,2,4,4-pentamethyl-20-(oxiranylmethyl)-7-oxa-3,20-diazadispiro[5.1.11.2]heneicosan-21-one, oligomerized 1-acetyl-2,2,4,4-tetramethyl-20-(oxiranylmethyl)-7-oxa-3,20-diaza-dispiro[5.1.11.2]heneicosan-21-one, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, 2,2,4,4-tetramethyl-7-oxa-3,20-diazadispiro-[5.1.11.2]heneicosan-21-one, 2,2,4,4-tetramethyl-7-oxa-21-oxo-3,20-diazadispiro-[5.1.11.2]heneicosane-3-propanoic acid dodecyl ester, 2,2,4,4-tetramethyl-7-oxa-21-oxo-3,20-diazadispiro-[5.1.11.2]heneicosane-3-propanoic acid tetradecyl ester, 2,2,3,4,4-pentamethyl-7-oxa-3,20-diazadispiro-[51.11.2]heneicosan-21-one, 2,2,3,4,4-pentamethyl-7-oxa-21-oxo-3,20-diaza-dispiro-[5.1.11.2]heneicosane-3-propanoic acid dodecyl ester, 2,2,3,4,4-pentamethyl-7-oxa-21-oxo-3,20-diazadispiro-[5.1.11.2]-heneicosane-3-propanoic acid tetradecyl ester, 3-acetyl-2,2,4,4-tetramethyl-7-oxa-3,20-diazadispiro-[5.1.11.2]heneicosane-21-one, 3-acetyl-2,2,4,4-tetramethyl-7-oxa-21-oxo-3,20-diaza-dispiro-[5.1.11.2]heneicosane-3-propanoic acid dodecyl ester, 3-acetyl-2,2,4,4-tetramethyl-7-oxa-21-oxo-3,20-diazadispiro-[5.1.11.2]heneicosane-3-propanoic acid tetradecyl ester, 1,1',3,3',5,5'-hexahydro-2,2',4,4',6,6'-hexaaza-2,2',6,6'-bismethano-7,8-dioxo-4,4'-bis(1,2,2,6,6-pentamethyl-4-piperidyl)biphenyl, poly-N,N'-bis-(2,2,6,6-tetramethyl-4-piperidyl)-1,8-diazadecylene, adduct of 2,2,6,6-tetramethyl-4-allyloxypiperidine and polymethylhydridosiloxane (molar mass up to 4000), adduct of 1,2,2,6,6-pentamethyl-4-allyloxypiperidine and polymethylhydridosiloxane (molar mass up to 4000), N,N'-diformyl-N,N'-bis(2,2,6,6-tetramethyl-4-piperidinyl)hexamethylenediamine, N,N'-diformyl-N,N'-bis(1,2,2,6,6-pentamethyl-4-piperidinyl)hexamethylenediamine, 5,11-bis-(2,2,6,6-tetramethyl-4-piperidinyl)-3,5,7,9,11,13-hexaazatetra-cyclo[7.4.0.0$^{2,7}$.1$^{3,13}$]tetradecane-8,14-dione, 5,11-bis(1,2,2,6,6-pentamethyl-4-piperidinyl)-3,5,7,9,11,13-hexaazatetra-cyclo[7.4.0.0$^{2,7}$.1$^{3,13}$]tetradecane-8,14-dione, [(4-methoxyphenyl)methylene]propanedioic acid bis(2,2,6,6-tetramethyl-4-piperidinyl) ester, [(4-methoxyphenyl)methylene]propanedioic acid bis-(1,2,2,6,6-pentamethyl-4-piperidinyl) ester, 2,4,6-tris(N-cyclohexyl-N-[2-(3,3,4,5,5-pentamethylpiperazinon-1-yl)ethyl]amino)-1,3,5-triazine, copolymer of styrene with methylstyrene and maleic anhydride reacted with 4-amino-2,2,6,6-tetramethylpiperidine and octadecylamine, copolymer of styrene with α-methylstyrene and maleic anhydride reacted with 4-amino-1,2,2,6,6-pentamethylpiperidine and octaclecylamine, polycarbonate with 2,2'-[(2,2,6,6-tetramethyl-4-piperidinyl)imino]bis[ethanol] as diol component, polycarbonate comprising 2,2'-(1,2,2,6,6-pentamethyl-4-piperidinyl)imino]bis[ethanol] as diol component, copolymer of maleic anhydride and an α-olefin up to $C_{30}$ reacted with 4-amino-2,2,6,6-tetramethylpiperidine, copolymer of maleic anhydride and an α-olefin up to $C_{30}$ reacted with 1-acetyl-4-amino-2,2,6,6-tetramethylpiperidine, copolymer of maleic anhydride and an α-olefin up to $C_{30}$ reacted with 4-amino-1,2,2,6,6-pentamethylpiperidine, and also the N-alkyl- and N-aryl-oxy derivatives of the abovementioned compounds with free NH groups on the piperidine, especially α-methylbenzyloxy and alkyloxy from $C_1$ to $C_{18}$.

2.7. Oxalamides, for example 4,4'-dioctyloxyoxanilide, 2,2'-diethoxyanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted and of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4',6-bis(2',4'-dimethylphenyl)-1,3,5-triazine, 2-(2,4-dihydroxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[4-dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine.

3. Metal deactivators, for example, N,N'-diphenyloxalamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl) 4,4'-biphenylenediphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyl-dibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite, tris(2-tert-butyl-4-thio(2'-methyl-4'-hydroxy-5'-tert-butyl)phenyl-5-methyl) phenyl phosphite, 2,2',2"-nitrilo[triethyl tris(3,3',5,5'-tetra-tert-butyl-1,1'-biphenyl-2,2'-diyl) phosphite], bis[2-methyl-4,6-bis(1,1-dimethylethyl)phenol]phosphorous acid ethyl ester.

5. Hydroxylamines, examples being N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhyd roxylamine, N,N-dioctadecylhyd roxylamine, N-hexadecyl-N-octadecylhydroxylamine, N-heptadecyl-N-octadecylhydroxylamine, N,N-dialkylhydroxylamines prepared from hydrogenated tallow fatty amine.

6. Nitrones, examples being N-benzyl alpha-phenyl nitrone, N-ethyl alpha-methyl nitrone, N-octyl alpha-heptyl nitrone, N-lauryl alpha-undecyl nitrone, N-tetradecyl alpha-tridecyl nitrone, N-hexadecyl alpha-pentadecyl nitrone, N-octadecyl alpha-heptadecyl nitrone, N-hexadecyl alphaheptadecyl nitrone, N-octadecyl alpha-pentadecyl nitrone, N-heptadecyl alpha-heptadecyl nitrone, N-octadecyl alpha-hexadecyl nitrone, nitrones derived from N,N-dialkylhydroxylamines prepared from hydrogenated tallow fatty amines.

7. Zeolites and hydrotalcites, such as ®DHT 4A. Hydrotalcites of this kind can be described by the formula

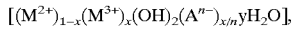
$[(M^{2+})_{1-x}(M^{3+})_x(OH)_2(A^{n-})_{x/n}yH_2O]$, where ($M^{2+}$) is Mg, Ca, Sr, Ba, Zn, Pb, Sn, Ni ($M^{3+}$) is Al, B, Bi $A^n$ is an anion of valency n n is an integer from 1–4 x is a value between 0 and 0.5 y is a value between 0 and 2

A is $OH^-$, $Cl^-$, $Br^-$, $I^-$, $ClO_4^-$, $CH_3COO^-$, $C_6H_5COO^-$, $CO_3^{2-}$, $SO_4^{2-}$, $(OOC-COO)^{2-}$, $(CHOHCOO)_2^{2-}$, $HO(CHOH)_4CH_2COO^-$, $C_2H_4(COO)_2^{2-}$, $(CH_2COO)_2^{2-}$, $CH_3CHOHCOO^-$, $SiO_3^{2-}$, $SiO_4^{4-}$, $Fe(CN)_6^{3-}$, $Fe(CN)_6^{4-}$, $BO_3^{3-}$, $PO_3^{3-}$, $HPO_4^{2-}$.

Preference is given to employing hydrotalcites in which ($M^{2+}$) is ($Ca^{2+}$), ($Mg^{2+}$) or a mixture of ($Mg^{2+}$) and ($Zn^{2+}$); ($A^{n-}$) is $CO_3^{2-}$, $BO_3^{3-}$, $PO_3^{3-}$; x has a value from 0 to 0.5 and y has a value from 0 to 2. It is also possible to employ hydrotalcites that can be described with the formula

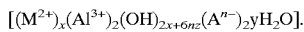
$[(M^{2+})_x(Al^{3+})_2(OH)_{2x+6nz}(A^{n-})_2yH_2O]$.

Here, ($M^{2+}$) is $Mg^{2+}$, $Zn^{2+}$, but more preferably $Mg^{2+}$. ($A^{n-}$) is an anion, in particular from the group consisting of $CO_3^{2-}$, $(OOC-COO)^{2-}$, $OH^-$ and $S^{2-}$, where n describes the valency of the ion. y is a positive number, more preferably between 0 and 5, especially between 0.5 and 5. x and z have positive values, which in the case of x are preferably between 2 and 6 and in the case of z should be less than 2. The hydrotalcites of the following formulae are to be regarded with particular preference:

$Al_2O_3 \times 6MgO \times CO_2 \times 12H_2O$,

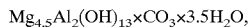
$Mg_{4.5}Al_2(OH)_{13} \times CO_3 \times 3.5H_2O$,

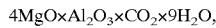
$4MgO \times Al_2O_3 \times CO_2 \times 9H_2O$,

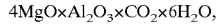
$4MgO \times Al_2O_3 \times CO_2 \times 6H_2O$,

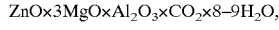
$ZnO \times 3MgO \times Al_2O_3 \times CO_2 \times 8-9H_2O$,

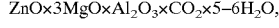
$ZnO \times 3MgO \times Al_2O_3 \times CO_2 \times 5-6H_2O$,

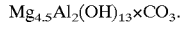
$Mg_{4.5}Al_2(OH)_{13} \times CO_3$.

Hydrotalcites are employed in the polymer preferably in a concentration of from 0.01 to 5% by weight, in particular from 0.2 to 3% by weight, based on the overall polymer formulation.

8. Thiosynergists, examples being dilauryl thiodipropionate and distearyl thiodipropionate.

9. Peroxide scavengers, examples being esters of β-thiodipropionic acid, for example the lauryl, stearyl, myristyl or tridecyl ester, mecaptobenzimidazole, the zinc salt of 2-mercaptobenzimidazole, zinc alkyldithiocarbamates, zinc dibutyidithiocarbamate, dioctadecyl monosulfide, dioctadecyl disulfide, pentaerythritol tetrakis(β-dodecyl-mercapto)propionate.

10. Polyamide stabilizers, examples being copper salts in combination with iodides and/or phosphorus compounds and salts of divalent manganese.

11. Basic costabilizers, examples being melamin, polyvinylpyrrolidone, dicyandiamide, triallyl cyanurate, urea derivatives, hydrazine derivatives, amines, polyamines, polyurethanes, alkali metal and alkaline earth metal salts of higher fatty acids, for example Ca stearate, Zn stearate, Mg behenate, Mg stearate, Na ricinoleate, K palmitate, antimony pyrocatecholate or tin pyrocatecholate, alkali metal and alkaline earth metal salts and also the zinc salt or the aluminum salt of lactic acid.

12. Nucleating agents, such as inorganic substances, examples being talc, metal oxides, such as titanium oxide or magnesium oxide, phosphates, carbonates or sulfates of, preferably, alkaline earth metals, organic compounds, such as mono- or polycarboxylic acids and also their salts, examples being 4-tert-butylbenzoic acid, adipic acid; diphenylacetic acid; sodium succinate or sodium benzoate; acetals of aromatic aldehydes and polyfunctional alcohols such as sorbitol, for example, such as 1,3-2,4-di(benzylidene)-D-sorbitol, 1,3-2,4-di(4-tolylidene)-D-sorbitol, 1,3-2,4-di(4-ethylbenzylidene)-D-sorbitol, polymeric compounds, such as ionic copolymers (ionomers), for example.

13. Fillers and reinforcing agents, examples being calcium carbonate, silicates, glass fibers, asbestos, talc, kaolin, mica, barium sulfate, metal oxides and metal hydroxides, carbon black, graphite, wood flour and other flours or fibers of other natural products, synthetic fibers.

14. Other additives, examples being plasticizers, lubricants, emulsifiers, pigments, rheological additives, catalysts, leveling assistants, optical brighteners, flameproofing agents, antistatics, blowing agents.

15. Benzofuranones and indolines, as described for example in U.S. Pat. No. 4,325,863, U.S. Pat. No. 4,338,244, U.S. Pat. No. 5,175,312; U.S. Pat. No. 5,216,052; U.S. Pat. No. 5,252,643, DE-A-4316611, DE-A-4316622, DE-A4316876, EP-A-0589839 or EP-A-0591102, or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuranon-2-one, 3,3'-bis[5,7-di-tert-butyl-3-(4-[2-hydroxyethoxy]phenyl)benzofuran-2-one, 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-diethyl-4-pivaloyloxyphenyl)-5,7-di-tert-butylbenzofuran-2-one.

The additives of the formula (III) or the combinations described above are incorporated into the organic material, preferably into the polymer, by the methods which are generally customary. Incorporation can take place, for example, by mixing or applying the compounds, with or without further additives, into or onto the polymer directly prior to, during or after polymerization, or into the polymer melt prior to or in the course of shaping. Incorporation can also take place by applying the dissolved or dispersed compounds to the polymer directly or by mixing them into a solution, suspension or emulsion of the polymer, with or without subsequent evaporation of the solvent. The compounds are also effective if they are introduced subsequently, in a separate processing step, into a ready-granulated polymer. The compounds of the formula (III) of the invention can also be added to the polymers to be stabilized in the form of a masterbatch which comprises these compounds, for example, in a concentration of from 1 to 75, preferably from 2.5 to 30% by weight.

The examples which follow are intended to illustrate the invention without limiting it in any way. All compounds of the formula (III) of the invention that were prepared were characterized by their $^{13}$C NMR spectra; the melting ranges of the oligomers prepared are indicated in the text and in Table 1.

EXAMPLE 1

47.0 g (0.06 mol) of 20,20'-(2-hydroxy-1,3-propanediyl) bis[2,2,4,4-tetramethyl-7-oxa-3,20-diazadispiro[5.1.11.2] heneicosan-21-one] (II') and 151.2 g (0.36 mol) of 2,2,4,4-tetramethyl-20-(oxiranylmethyl)-7-oxa-3,20-diazadispiro [5.1.11.2]heneicosan-21-one (I') are polymerized in vacuo for 6 h at 200° C. In the course of this reaction the solids melt and a colorless, viscous melt is formed. After the reaction material has cooled, the brittle mixture is forced from the flask with liquid nitrogen and pulverized. The melting range of the oligomer is from 1883 to 230° C.

Table 1
Proportions of the Starting Materials (I') and (II'), and Melting Ranges of the Oligomers Prepared

TABLE 1

Proportions of the starting materials (I') and (II"), and melting ranges of the oligomers prepared

| Example: | (I') [mol] | (II") [mol] | Melting range of the oligomer [° C.] |
|---|---|---|---|
| 2 | 0.24 | 0.12 | 162–212 |
| 3 | 0.30 | 0.10 | 171–219 |
| 4 | 0.32 | 0.08 | 179–220 |
| 5 | 0.55 | 0.11 | 180–221 |

EXAMPLE 6

Light Stabilizing Action in Polyethylene With and Without Chemical Contact 100 parts by weight of unstabilized polyethylene (®Polyethylen LE 4510 from Borealis) were mixed together with 0.1 part by weight of pentaerythrityl tetrakis[3-(3,5-di-tert-butyl-4-hydroxyphenyl)propionate] (®Hostanox O10) and 0.05 part by weight of tris(2,4-di-tert-butylphenyl) phosphite (®Hostanox PAR 24). This base formulation is granulated twice with 0.2 part by weight of the stabilizer from Example 1, alone or in combination with 0.1 part by weight of the hydrotalcite ®DHT 4A or with a mixture of 0.05 part by weight of zinc oxide and 0.05 part by weight of calcium stearate, using a Brabender mixer having a single screw, at 125 rpm, heating zone 150/180/220° C., and in this way is intensively homogenized. This base mixture is melted in a twin-screw extruder and then granulated, and blown films with a thickness of 200 μm are produced from the granules. The test specimens obtained in this way are exposed in an accelerated weathering device (®Xenotest 1200). The criterion used for the stability of the film was the change in the carbonyl index during the exposure period, said index being measured at regular intervals (every 200 h) and being determined in accordance with the formula $CO = E_{172}(/E_{2020}$ (E=extinction (absorbance)); the exposure end point is set by the increase of the carbonyl index by one unit. For purposes of comparison, a film was tested under the same conditions but without the addition of the stabilizer of the invention from Example 1. The experimental results are collated in Table 1'.

Table 1'
Degradation of Stabilized Polyethylene

TABLE 1'

Degradation of stabilized polyethylene

| Stabilizer used in addition to base stabilization | Concentration in % by weight | Hours until $\Delta CO > 1$ is reached |
|---|---|---|
| a) None | — | 310 |
| b) Stabilizer from Example 1 | 0.2 | 1010 |
| c) Zinc oxide and calcium stearate | 0.05/0.05 | 580 |
| d) Hydrotalcite (DHT 4a) | 0.1 | 520 |
| e) Stabilizer from Example 1 Zinc oxide and calcium stearate | 0.2 0.05/0.05 | 2240 |
| f) Stabilizer from Example 1 Hydrotalcite (DHT 4a) | 0.2 0.1 | 1610 |

The base-stabilized film reaches the criterion $\Delta CO>1$, which describes the polymer degradation, after 310 h. The stabilizing action of the additionally employed stabilizers is given by the number of hours beyond the 310 h. For example, 0.2% by weight of stabilizer from Example 1 make a st abilizing contribution of (1010–310)=700 hours. The stabilizing contribution of 0.1% by weight of hydrotalcite is (520–310)=210 hours. An additive stabilizing effect would lead, with a combination of the stabilizer from Example 1 and hydrotalcite (DHT 4a), to a total stabilization of (310 h+700 h+210 h)=1220 h. In fact, however, the combination of the stabilizer from Example 1 with hydrotalcite (DHT 4a) leads to a total stabilization of 1610 h; in other words, the combination is synergistic. A synergism is observed in the same manner for combination e).

EXAMPLE 7

Light Stabilizing Action in Polypropylene Sheets 100 parts by weight of unstabilized polypropylene ®Hostalen PPK 0160 were mixed together with 0.1 part by weight of pentaerythrityl tetrakis[3-(3,5-di-tert-butyl-4-hydroxyphenyl)propionate] (®Hostanox O 10) and 0.1 part by weight of calcium stearate (Greven). This base formulation is granulated twice with 0.1 part by weight of the stabilizer from Example 1, or with a combination of the stabilizer from Example 1 (0.05% by weight) and the monomeric HALS stabilizers indicated in Tab. 2 (0.05% by weight) with a Leistritz twin-screw extruder (counterrotating screws, heating zones 210° C., 22° C., 230° C., 240° C.). The granules are subsequently processed to give injection-molded plates with a thickness of 2 mm (Toshiba twin-screw extruder, counter rotating screws, heating zones 21° C., 220° C., 230° C., 240° C.). The test specimens obtained in this way are exposed in an accelerated weathering device (®Xenotest 1200). The criterion employed for the stability of the test specimens was the increase in the coloration, which was measured at regular intervals (every 150 h). For purposes of comparison, a sheet was tested under the same conditions but without the addition of the stabilizer of the invention from Example 1.

Table 2
Discoloration of Stabilized Polypropylene (evaluated visually using a microscope and the following gradations of assessment: 0=none, 1=trace, 2=little, 3=some, 4=marked, 5=significant, 6=severe).

| Stabilizer employed in addition to base stabilization | | Concentration in % by weight | 290 h | 508 h | 674 h |
|---|---|---|---|---|---|
| a) | None | — | 0 | 0 | 6 |
| b) | Stabilizer from Example 1 | 0.1 | 0 | 0 | 2 |
| c) | Stabilizer A* | 0.1 | 0 | 1 | 3 |
| d) | Stabilizer B** | 0.1 | 0 | 0 | 1 |
| e) | Stabilizer from Example 1<br>Stabilizer A* | 0.05<br>0.05 | 0 | 0 | 0 |
| f) | Stabilizer from Example 1<br>Stabilizer B** | 0.05<br>0.05 | 0 | 0 | 0 |

*bis(2,2,6,6-Tetramethyl-4-piperidyl) sebacate (®Tinuvin 770, CIBA Specialty Chem.)
**2,2,4,4-Tetramethyl-7-oxa-3,20-diazadispiro-[5.1.11.2] heneicosan-21-one (®Hostavin N20, Clariant GmbH)

The table demonstrates that the stabilizing action of a combination of stabilizer from Example 1 with monomeric light stabilizers based on sterically hindered amines is better than could have been expected from the sum of the individual components.

EXAMPLE 8

Light Stabilizing Action in Compression-molded Polypropylene Films 100 parts by weight of unstabilized polypropylene ®Hostalen PPK 0160 were mixed together with 0.1 part by weight of pentaerythrityl tetrakis[3-(3,5-di-tert-butyl-4-hydroxyphenyl)propionate] (®Hostanox O 10) and 0.1 part by weight of calcium stearate. This base formulation is kneaded with 0.1 part by weight of the stabilizer from Example 1, or with a combination of the stabilizer from Example 1 (0.05% by weight) and the polymeric HALS stabilizer indicated in Tab. 3 (0.05% by weight) in a Brabender mixer at 200° C. and 20 rpm for 10 min, and in this way is intensively homogenized. This base mixture is used to produce compression-molded films with a thickness of 100 µm. The test specimens obtained in this way are exposed in an accelerated weathering device (®Xenotest 1200). The criterion employed for the stability of the test specimens was the change in the carbonyl index during exposure, which was measured at regular intervals (every 150 h). The carbonyl index CO here was determined in accordance with the formula $CO=E_{1720}/E_{2020}$ (E=extinction (absorbance)); the exposure end point is set by the increase in the carbonyl index by one unit. For purposes of comparison, a film was tested under the same conditions but without the addition of the stabilizer of the invention from Example 1.

Table 3
Degradation of Stabilized Polypropylene

TABLE 3

Degradation of stabilized polypropylene

| Stabilizer used in addition to base stabilization | | Concentration in % by weight | Hours until ΔCO > 1 is reached |
|---|---|---|---|
| a) | None | — | 350 |
| b) | Stabilizer from Example 1 | 0.1 | 900 |
| c) | Stabilizer C* | 0.1 | 700 |
| d) | Stabilizer from Example 1<br>Stabilizer C | 0.05<br>0.05 | 896 |

*Polymer of butanedioic acid with 4-hydroxy-2,2,6,6-tetramethyl-1-(2-hydroxyethyl)piperidine (®Tinuvin 622, CIBA Specialty Chem.)

The base-stabilized film reaches the criterion ΔCO>1, which describes the polymer degradation, after 350 h. The stabilizing action of the additionally employed stabilizers results from the number of hours beyond the 350 h. Thus 0.1% by weight of stabilizer from Example1 make a stabilizing contribution of (900 h−350 h)=550 h. The stabilizing contribution of the stabilizer C is (700 h−350 h)=350 h. In the evaluation of the results it must be borne in mind that the concentrations of the stabilizers in Example d were reduced to half. An additive stabilizing effect would lead, with a combination of the stabilizer from Example 1 with stabilizer C, to a total stabilization of (350 h+550/2 h)=800 h. In fact, however, the combination of the stabilizer from Example 1 with stabilizer C leads to a total stabilization of 896 h; in other words, the combination is synergistic.

EXAMPLE 9

Light Stabilizing Action in Compression-molded Polypropylene Films 100 parts by weight of unstabilized polypropylene ®Hostalen PPK 0160 were mixed together with 0.1 part by weight of pentaerythrityl tetrakis[3-(3,5-di-tert-butyl-4-hydroxyphenyl)propionate] (®Hostanox O 10) and 0.1 part by weight of calcium stearate. This base formulation is kneaded with 0.1 part by weight of the stabilizer from Example 1, or with a combination of the stabilizer from Example 1 (0.05% by weight) and the UV absorber (0.05% by weight) indicated in Tab. 3 in a Brabender mixer at 200° C. and 20 rpm for 10 min, and in this way is intensively homogenized. This base mixture is used to produce compression-molded films with a thickness of 100 µm. The test specimens obtained in this way are exposed in an accelerated weathering device (®Xenotest 1200). The criterion employed for the stability of the test specimens was the change in the carbonyl index during exposure, which was measured at regular intervals (every 150 h). The carbonyl index CO here was determined in accordance with the formula $CO=E_{1720}/E_{2020}$ (E=extinction (absorbance)); the exposure end point is set by the increase in the carbonyl index by one unit. For purposes of comparison, a film was tested under the same conditions but without the addition of the stabilizer of the invention from Example 1.

Table 4
Degradation of Stabilized Polypropylene

TABLE 4

Degradation of stabilized polypropylene

| Stabilizer used in addition to base stabilization | | Concentration in % by weight | Hours until ΔCO > 1 is reached |
|---|---|---|---|
| a) | None | — | 350 |
| b) | Stabilizer from Example 1 | 0.1 | 900 |
| c) | Stabilizer D* | 0.1 | 458 |
| d) | Stabilizer from Example 1<br>Stabilizer D* | 0.05<br>0.05 | 710 |

*Benzotriazole stabilizer (®Tinuvin P, CIBA Specialty Chem.)

The base-stabilized film reaches the criterion ΔCO>1, which describes the polymer degradation, after 350 h. The stabilizing action of the additionally employed stabilizers results from the number of hours beyond the 350 h. Thus 0.1% by weight of stabilizer from Example1 make a stabilizing contribution of (900 h−350 h)=550 h. The stabilizing contribution of the stabilizer D is (458 h−350 h)=108 h. In the evaluation of the results it must be borne in mind that the concentrations of the stabilizers in Example d were reduced to half. An additive stabilizing effect would lead, with a combination of the stabilizer from Example 1 with stabilizer C, to a total stabilization of (350 h+550/2 h+108/2 h)=679 h. In fact, however, the combination of the stabilizer from Example 1 with stabilizer C leads to a total stabilization of 710 h; in other words, the combination is synergistic.

EXAMPLE 10
Light Stabilizing Action in Compression-molded Polypropylene Films 100 parts by weight of unstabilized polypropylene ®Hostalen PPK 0160 were mixed together with 0.1 part by weight of pentaerythrityl tetrakis[3-(3,5-di-tert-butyl-4-hydroxyphenyl)propionate] (®Hostanox O 10) and 0.1 part by weight of calcium stearate. This base formulation is kneaded with 0.1 part by weight of the stabilizer from Example 1, or with a combination of the stabilizer from Example 1 (0.05% by weight) and the sterically hindered phosphites indicated in Tab. 5 (0.05% by weight) in a Brabender mixer at 200° C. and 20 rpm for 10 min, and in this way is intensively homogenized. This base mixture is used to produce compression-molded films with a thickness of 100 μm. The test specimens obtained in this way are exposed in an accelerated weathering device (®Xenotest 1200). The criterion employed for the stability of the test specimens was the change in the carbonyl index during exposure, which was measured at regular intervals (every 150 h). The carbonyl index CO here was determined in accordance with the formula $CO=E_{1720}/E_{2020}$ (E=extinction (absorbance)); the exposure end point is set by the increase in the carbonyl index by one unit. For purposes of comparison, a film was tested under the same conditions but without the addition of the stabilizer of the invention from Example 1.

TABLE 5
Degradation of stabilized polypropylene

| Stabilizer used in addition to base stabilization | Concentration in % by weight | Hours until ΔCO > 1 is reached |
|---|---|---|
| a) None | — | 300 |
| b) Stabilizer from Example 1 | 0.1 | 900 |
| c) Stabilizer E* | 0.1 | 460 |
| d) Stabilizer F** | 0.1 | 400 |
| e) Stabilizer from Example 1<br>Stabilizer E* | 0.05<br>0.05 | 820 |
| f) Stabilizer from Example 1<br>Stabilizer F** | 0.05<br>0.05 | 700 |

*Stabilizer E: bis(2,4-di-tert-butylphenyl) pentaerythritol diphosphite (®Weston 626, Borg Warner)
**Stabilizer F: Tris(2,4-di-tert-butylphenyl) phosphite (Hostanox PAR 24, Clariant GmbH)

The base-stabilized film reaches the criterion ΔCO>1, which describes the polymer degradation, after 300 h. The stabilizing action of the additionally employed stabilizers results from the number of hours beyond the 300 h. For example, 0.1% by weight of stabilizer from Example 1 make a stabilizing contribution of (900 h–300 h)=600 h. The stabilizing contribution of the stabilizer E is (460 h–300 h)=160 h. In the evaluation of the results it must be borne in mind that the concentrations of the stabilizers in Examples e and f were reduced to half. An additive stabilizing effect would lead, with a combination of the stabilizer from Example 1 with stabilizer E, to a total stabilization of (300 h+600/2 h+160/2 h)=680 h. In fact, however, the combination of the stabilizer from Example 1 with stabilizer E leads to a total stabilization of 820 h; in other words, the combination is synergistic.

EXAMPLE 11
Hydrolysis of Phosphites (weight increase) as a Function of Time The hydrolysis of phosphites involves the uptake of water (from atmos-pheric humidity, for example). Thus phosphites absorb water firstly in the course of storage and secondly also in incorporated form in the polymer, and become ineffective as hydrolysis increases. This hydrolysis can be made visible by observing the water uptake of a phosphite by way of its weight increase. For this purpose, an amount of 125 g of bis(2,4-di-tert-butylphenyl) pentaerythritol diphosphite (®Weston 626, Borg Warner) is stored open in a climatically controlled chamber at 23° C. and a relative atmospheric humidity of 50%. With the aim of demonstrating the reduction in the propensity of this phosphite to undergo hydrolysis as a result of the novel stabilizer from Example 1, a second sample (this time a homo-geneous mixture of 125 g of bis(2,4-di-tert-butylphenyl) pentaerythritol diphosphite and 5 g of the stabilizer from Example 1) is stored likewise open in a climatically controlled chamber at 23° C. and a relative atmospheric humidity of 50%. Both samples were in the form of crystal powders.

Over the course of 21 days bis(2,4-di-tert-butylphenyl) pentaerythritol diphosphite absorbs an amount of 3 g of water; the mixture of bis(2,4-di-tert-butylphenyl) pentaerythritol diphosphite and the stabilizer from Example 1, however, absorbs only 2 g of water. This therefore demonstrates that the stabilizer from Example 1 reduces markedly the propensity of phosphites to undergo hydrolysis.

SUMMARY

The compounds of the formula (III) of the invention act outstandingly as stabilizers for polymeric material. Mixtures of the compounds of the formula (III) of the invention with monomeric HALS, polymeric HALS and/or phosphites and/or acid scavengers have a stabilizing action on organic material and exhibit an improved profile of properties with respect to the individual components; for example, synergies in the photoprotective effect.

What is claimed is:
1. A compound of the formula (III),

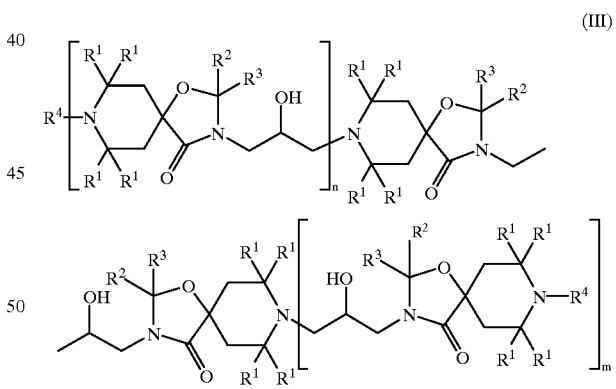

(III)

in which n and m independently of one another are a number from 0 to 100, but n and m cannot both be 0, $R^1$ is hydrogen, $C_5$–$C_7$-cycloalkyl, or a $C_1$–$C_{12}$-alkyl group, $R^2$ and $R^3$ independently of one another are a hydrogen atom or a $C_1$–$C_{18}$-alkyl group or, together with the carbon atom connecting them, are a 5- to 13-membered ring of carbon atoms or, together with the carbon atom connecting them, are a group of the formula (IV)

(IV)

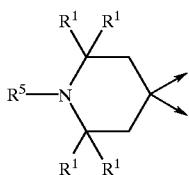

R⁴ and R⁵ independently of one another are either hydrogen or a $C_1$–$C_{22}$-alkyl group, an oxygen radical O*, —OH, —NO, —CH₂CN, benzyl, allyl, a $C_1$–$C_{30}$-alkyloxy group, a $C_5$–$C_{12}$-cycloalkyloxy group, a $C_6$–$C_{10}$-aryloxy group, a $C_7$–$C_{20}$-arylalkyloxy group, a $C_3$–$C_{10}$-alkenyl group, a $C_3$–$C_6$-alkynyl group, a $C_1$–$C_{10}$-acyl group, halogen or $C_7$–$C_9$-phenylalkyl which is unsubstituted or substituted on the phenyl ring by $C_1$–$C_4$-alkyl.

2. The compound as claimed in claim 1, wherein n and m independently of one another are a number from 0 to 10, but n and m cannot both be 0, R¹ is hydrogen, $C_6$-cycloalkyl, or a $C_1$–$C_4$-alkyl group, R² and R³ independently of one another are a hydrogen atom or a $C_1$–$C_8$-alkyl group, or, together with the carbon atom connecting them, are a 6- to 12-membered ring of carbon atoms or, together with the carbon atom connecting them, are a group of the formula (IV), R⁴ and R⁵ independently of one another are either hydrogen or a $C_1$–$C_5$-alkyl group, an oxygen radical O*, —OH, —NO, —CH₂CN, benzyl, allyl, a $C_1$–$C_{10}$-alkyloxy group, a $C_5$–$C_6$-cycloalkyloxy group, a $C_6$–$C_7$-aryloxy group, a $C_7$–$C_{10}$-arylalkyloxy group, a $C_3$–$C_6$-alkenyl group, a $C_3$–$C_6$-alkynyl group, a $C_1$–$C_4$-acyl group, halogen or $C_7$–$C_9$-phenylalkyl which is unsubstituted or substituted on the phenyl ring by $C_1$–$C_2$-alkyl.

3. The compound as claimed in claim 1, wherein n and m independently of one another are a number from 0 to 5, but n and m cannot both be 0, R¹ is methyl, R² and R³, together with the carbon atom connecting them, are a 12-membered ring of carbon atoms or, together with the carbon atom connecting them, are a group of the formula (IV), R⁴ and R⁵ independently of one another are hydrogen, methyl, acetyl, octyloxy or cyclohexyloxy.

4. The compound as claimed in claim 1, which is a stabilizer against the damaging effect of oxygen, light and heat.

5. A process for preparing a compound of the formula (III) as claim 1, which comprises reacting a compound of the formula (I) with a compound of the formula (II)

(I)

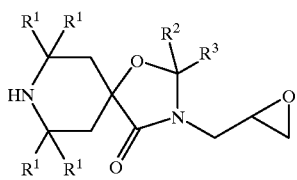

(II)

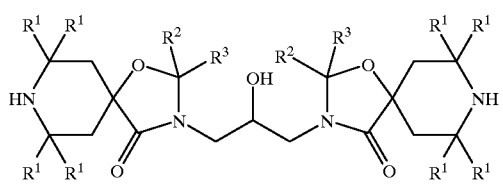

in which R¹ to R⁴ are as defined in claim 1 with or without solvent and with or without catalyst in a molar ratio of from 1:1 to 100:1 and at from 100 to 300° C.

6. The process as claimed in claim 5, wherein the reaction takes place without solvent and without catalyst in vacuo at from 120 to 250° C.

7. A method of using a compound of the formula (III), (III)

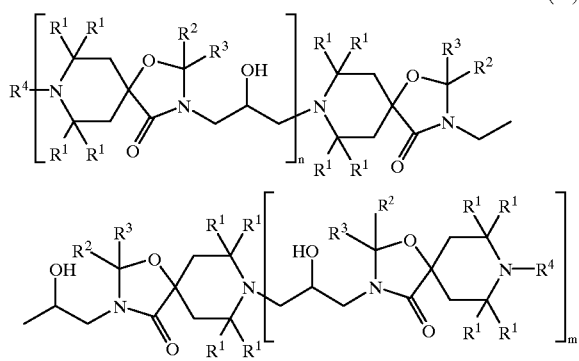

in which n and m independently of one another are a number from 0 to 100, but n and m cannot both be 0, R¹ is hydrogen, $C_5$–$C_7$-cycloalkyl, or a $C_1$–$C_{12}$-alkyl group, R² and R³ independently of one another are a hydrogen atom or a $C_1$–$C_{18}$-alkyl group or together with the carbon atom connecting them, are a 5- to 13-membered ring of carbon atoms or, together with the carbon atom connecting them, are a group of the formula (IV)

(IV)

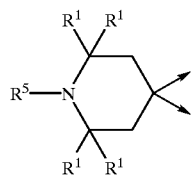

R⁴ and R⁵ independently of one another are either hydrogen or a $C_1$–$C_{22}$-alkyl group, an oxygen radical O*, —OH, —NO, —CH₂CN, benzyl, allyl, a $C_1$–$C_{30}$-alkyloxy group, a $C_5$–$C_{12}$-cycloalkyloxy group, a $C_6$–$C_{10}$-aryloxy group, a $C_7$–$C_{20}$-arylalkyloxy group, a $C_3$–$C_{10}$-alkenyl group, a $C_3$–$C_6$-alkynyl group, a $C_1$–$C_{10}$-acyl group, halogen or $C_7$–$C_9$-phenylalkyl which is unsubstituted or substituted on the phenyl ring by $C_{14}$-alkyl;

for stabilizing organic material against damage by light and heat, said method comprising adding the stabilizer in a concentration of 0.001 to 5% by weight, based on the stabilized organic material.

8. A mixture of a compound of the formula (III) as claimed in claim 1 with one or more stabilizers based on sterically hindered amines of the formulae A1 to A10

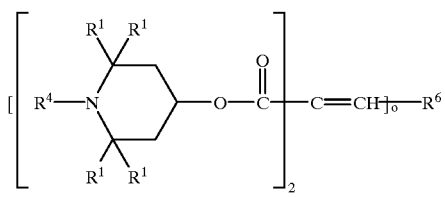

A1 in which

R$^1$ and R$^4$ are as defined in claim 1,

R$^6$ is an aromatic radical substituted one or more times by hydrogen, C$_1$–C$_4$-alkyl, C$_1$–C$_4$-alkoxy, halogen, cyano, carboxyl, nitro, amino, C$_1$–C$_4$-alkylamino, C$_1$–C$_4$-dialkylamino, or acyl, o is 1 or 2,

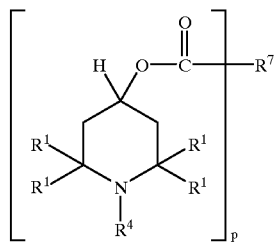

A2 in which

R$^1$ and R$^4$ are as defined in claim 1, p=1 or 2 and if p=1,

R$^7$ is C$_1$–C$_{22}$-alkyl, C$_2$–C$_{18}$-oxaalkyl, C$_2$–C$_{18}$-thiaalkyl, C$_2$–C$_{18}$-azaalkyl or C$_2$–C$_8$-alkenyl;

if p=2,

R$^7$ is C$_1$–C$_{22}$-alkylene, C$_2$–C$_{18}$-oxaalkylene, C$_2$–C$_{18}$-thiaalkylene, C$_2$–C$_{18}$-azaalkylene or C$_2$–C$_8$-alkenylene;

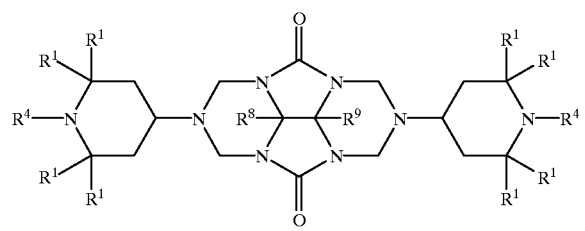

A3 in which

R$^1$ and R$^4$ are as defined in claim 1,

R$^8$ and R$^9$ independently of one another are hydrogen, C$_1$–C$_6$-alkyl, C$_7$–C$_{12}$-aralkyl, -aryl or carboxylic ester, R$^8$ and R$^9$ together are a tetra- or pentamethyl group;

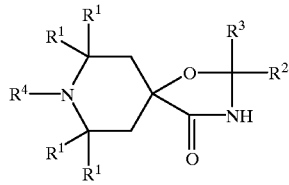

A4

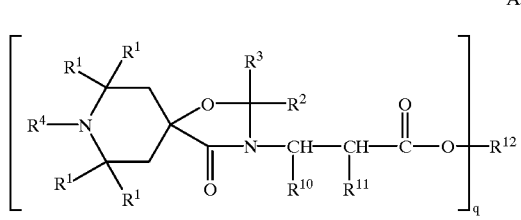

A5 in which

R$^1$, R$^2$, R$^3$ and R$^4$ are as defined in claim 1, q is a number 1 or 2, R$^{10}$ is hydrogen, methyl, phenyl or carb-C$_1$–C$_{21}$-alkoxy, R$^{11}$ is hydrogen or methyl, R$^{12}$, if q=1, is hydrogen, C$_1$–C$_{21}$-alkyl, C$_2$–C$_{22}$-alkenyl, C$_5$–C$_{12}$-cycloalkyl, a radical of the formula

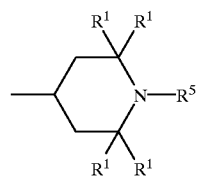

where

R$^1$ and R$^5$ are as defined in claim 1, and

R$^{12}$, if q=2, is C$_1$–C$_{18}$-alkylene, C$_5$–C$_9$-cycloalkylene or arylene;

A6 where $R^1$, $R^4$, $R^7$ and p are as defined above;

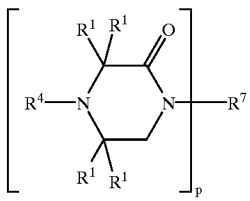
(A7)

where $R^1$, $R^4$, $R^7$ and p are as defined above;

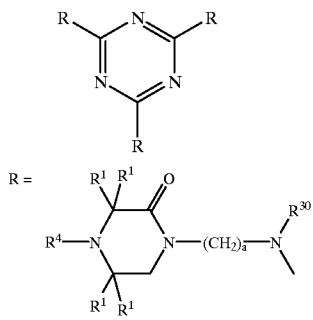
(A8)

where $R^1$, $R^4$ are as defined above, $R^{30}$ is hydrogen, $C_1$–$C_{12}$-alkyl, $C_5$–$C_{12}$-cycloalkyl, phenyl or $C_7$–$C_9$-phenylalkyl, and a is a number from 1 to 10;

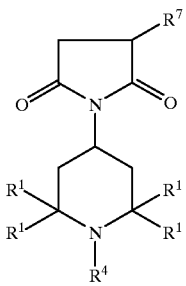
(A9)

where $R^1$ and $R^4$ are as defined above and $R^7$ is as defined for p=1 in the formula A2;

a product A10 obtainable by reacting a polyamine of the formula A10a with formula A10b:

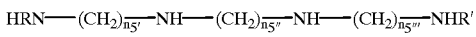
(A10a)

R and R' = H, CH$_3$

-continued

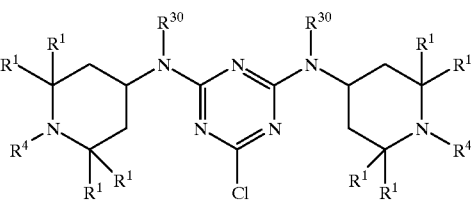
(A10b)

where $R^1$, $R^4$ and $R^{30}$ are as defined above, $n_{5'}$, $n_{5''}$ and $n_{5'''}$ independently of one another are a number from 2 to 12.

9. The mixture as claimed in claim 8, wherein n and m independently of one another are a number from 0 to 10, but n and m cannot both be 0, $R^1$ is hydrogen or a $C_1$–$C_4$-alkyl group, $R^2$ and $R^3$ independently of one another are a hydrogen atom or a $C_1$–$C_8$-alkyl group or, together with the carbon atom connecting them, are a 6- to 12-membered ring of carbon atoms or, together with the carbon atom connecting them, are a group of the formula (IV), $R^4$ and $R^5$ independently of one another are either hydrogen or a $C_1$–$C_5$-alkyl group, an oxygen radical O*, —OH, —NO, —CH$_2$CN, benzyl, allyl, a $C_1$–$C_{10}$-alkyloxy group, a $C_5$–$C_6$-cycloalkyloxy group, a $C_6$–$C_7$-aryloxy group; a $C_7$–$C_{10}$-arylalkyloxy group, a $C_3$–$C_6$-alkenyl group, a $C_3$–$C_6$-alkynyl group, a $C_1$–$C_4$-acyl group, halogen or $C_7$–$C_9$-phenylalkyl which is unsubstituted or substituted on the phenyl ring by $C_1$–$C_2$-alkyl, $R^7$ is a straight chain $C_1$–$C_{10}$-alkylene (if p=2); $C_1$–$C_{12}$-alkyl (if p=1)

$R^8$ and $R^9$ independently of one another are hydrogen, $C_1$–$C_2$-alkyl, $C_7$–$C_8$-arylalkyl, aryl- or carboxylic ester, $R^{10}$ is hydrogen, methyl, phenyl or $C_1$–$C_2$-alkoxy, $R^{11}$ is hydrogen or methyl, $R^{12}$, if q=1, is hydrogen, $C_1$–$C_{16}$-alkyl, $C_2$–$C_{16}$-alkenyl, $C_5$–$C_6$-cycloalkyl, a radical of the formula

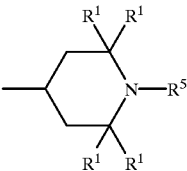

$R^{12}$, if q=2, is $C_1$–$C_{16}$-alkylene, $C_5$–$C_6$-cycloalkylene or arylene, $R^{30}$ is hydrogen, $C_1$–$C_8$-alkyl, $C_5$–$C_7$-cycloalkyl, phenyl or $C_7$–$C_8$-phenylalkyl, a is 1 to 5, o 1 and p 2 to 5.

10. The mixture as claimed in claim 8, wherein n and m independently of one another are a number from 0 to 5, but n and m cannot both be 0, $R^1$ is methyl, $R^2$ and $R^3$, together with the carbon atom connecting them, are a 12-membered ring of carbon atoms or, together with the carbon atom connecting them, are a group of the formula (IV), $R^4$ and $R^5$ independently of one another are hydrogen, methyl, acetyl, octyloxy or cyclohexyloxy, $R^6$ is p-methoxyphenyl, $R^7$ is octamethylene, hexamethylene or ethylene (if p=2), dodecyl (if p=1), $R^8$ and $R^9$ are hydrogen, $R^{10}$ is hydrogen, $R^{11}$ is hydrogen, $R^{12}$ is dodecamethylene or tetradecamethylene, $R^{30}$ is cyclohexyl or n-butyl, a is 2, o is 1, p is 2 and q is 1.

11. A mixture as claimed in claim 8, wherein the HALS compounds of the mixture comprising compounds of the formula (III) are the following substances:

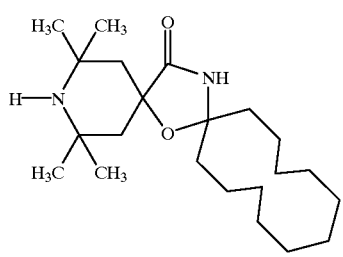
A'1

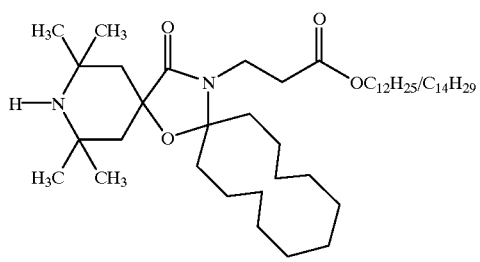
A'2

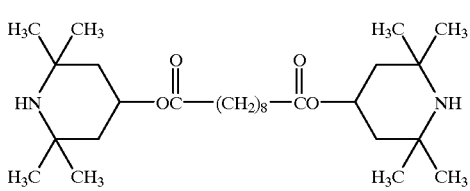
A'3

-continued

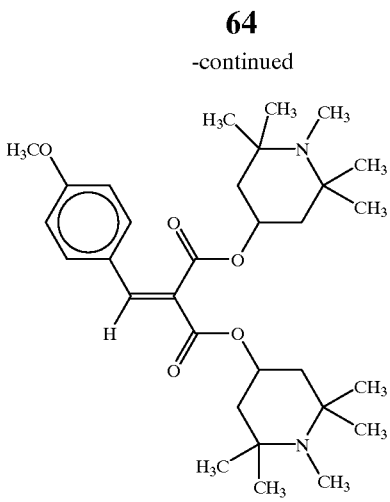
A'4

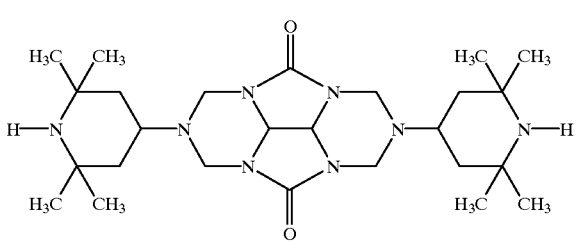
A'5

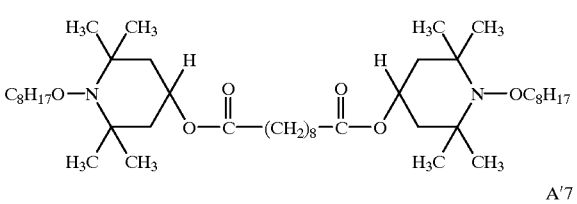
A'6

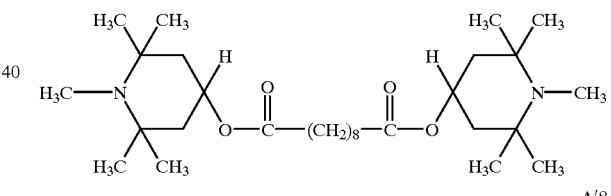
A'7

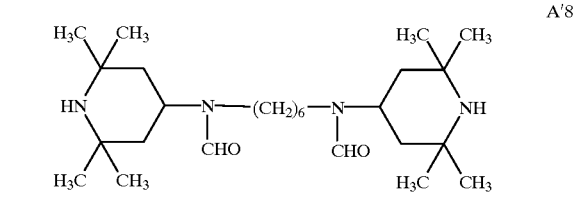
A'8

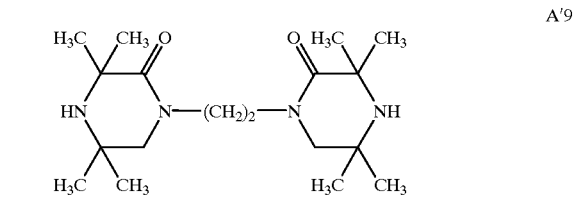
A'9

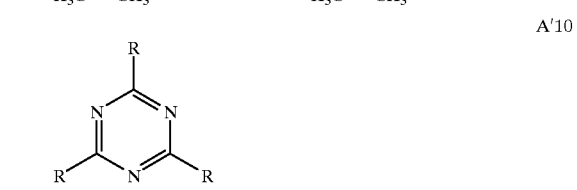
A'10

-continued

R = 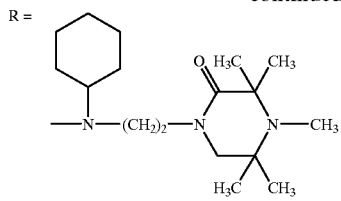

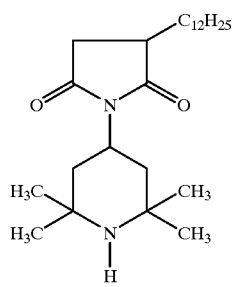 A'11

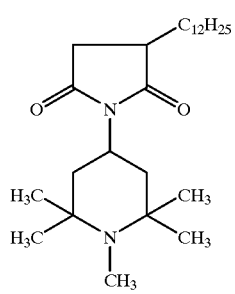 A'12

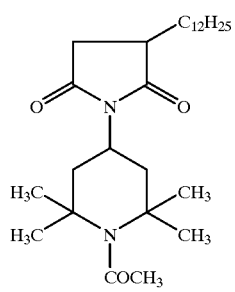 A'13

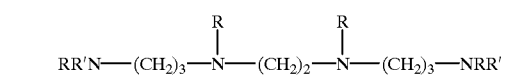 A'14 where R = and R' = H, CH$_3$

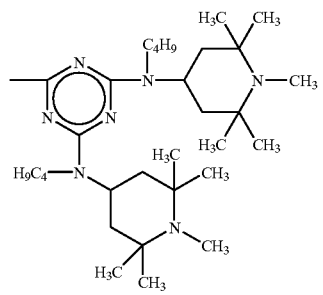

12. A mixture of a compound of the formula (III) as claimed in claim 1 with one or more polymeric HALS compounds of the formulae B1 to B7

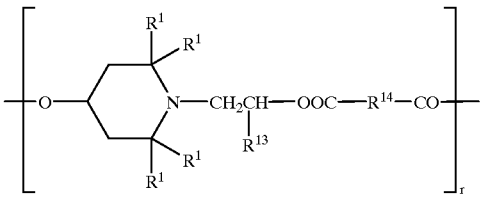 B1 in which

R$^1$ is as defined in claim 1,

R$^{13}$ is hydrogen or methyl,

R$^{14}$ is a direct bond or C$_1$–C$_{10}$-alkylene and r is a number from 2 to 50;

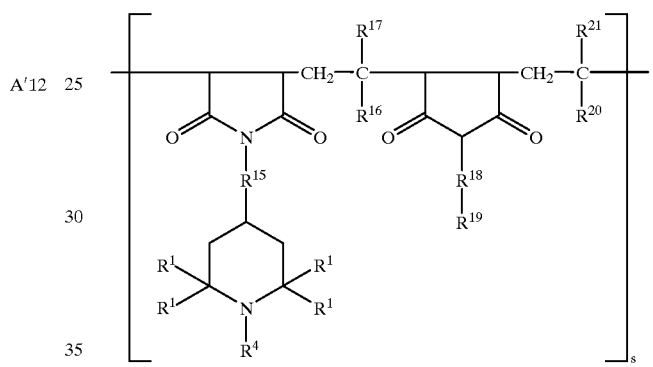 B2 where

R$^1$ and R$^4$ are as defined in claim 1,

R$^{15}$ and R$^{18}$ independently of one another are a direct bond or a group —N(R$^{22}$)—CO—R$^{23}$—CO—N(R$^{24}$)—, R$^{22}$ and R$^{24}$ independently of one another are hydrogen, C$_1$–C$_8$-alkyl, C$_5$–C$_{12}$-cycloalkyl, phenyl, C$_7$–C$_9$-phenylalkyl, or a group of the formula

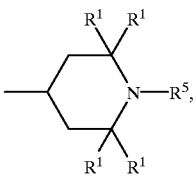 B2a

R$^{23}$ is a direct bond or C$_1$–C$_4$-alkylene,

R$^{16}$, R$^{17}$, R$^{20}$, R$^{21}$ independently of one another are hydrogen, C$_1$–C$_{30}$-alkyl, C$_5$–C$_{12}$-cycloalkyl, phenyl, or a group of the formula B2a, R$^{19}$ is hydrogen, C$_1$–C$_{30}$-alkyl, C$_5$–C$_{12}$-cycloalkyl, C$_7$–C$_9$-phenylalkyl, phenyl or a group of the formula B2a and s is a number from 1 to 50;

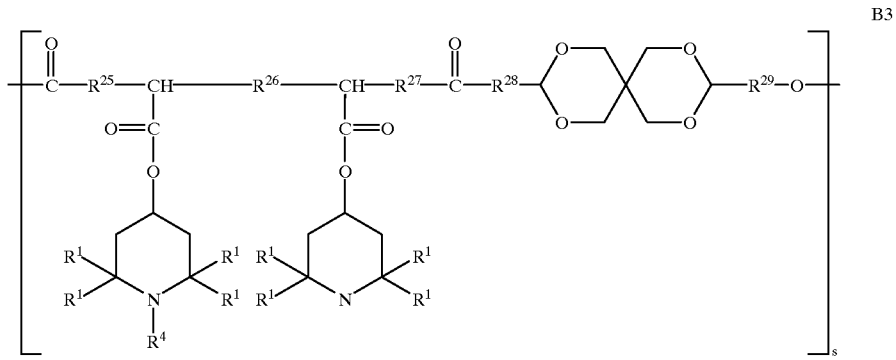

where

R$^1$, R$^4$ and s are as defined above,

R$^{25}$, R$^{26}$, R$^{27}$, R$^{28}$ and R$^{29}$ independently of one another are a direct bond or C$_1$–C$_{10}$-alkylene;

a product B4 obtainable by reacting a polyamine of the formula B4a with cyanuric chloride and then reacting the resulting product with a compound of the formula B4b,

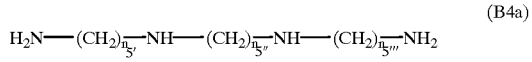
(B4a)

(B4b)

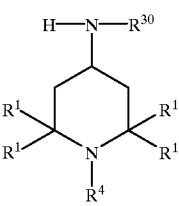

where

R$^1$ and R$^4$ are as defined in claim 1, n$_{5'}$, n$_{5''}$ and n$_{5'''}$ independently of one another are a number from 2 to 12, R$^{30}$ is hydrogen, C$_1$–C$_{12}$-alkyl, C$_5$–C$_{12}$-cycloalkyl, phenyl or C$_7$–C$_9$-phenylalkyl; where B4 is a compound of the formula B4-1, B4-2, B4-3

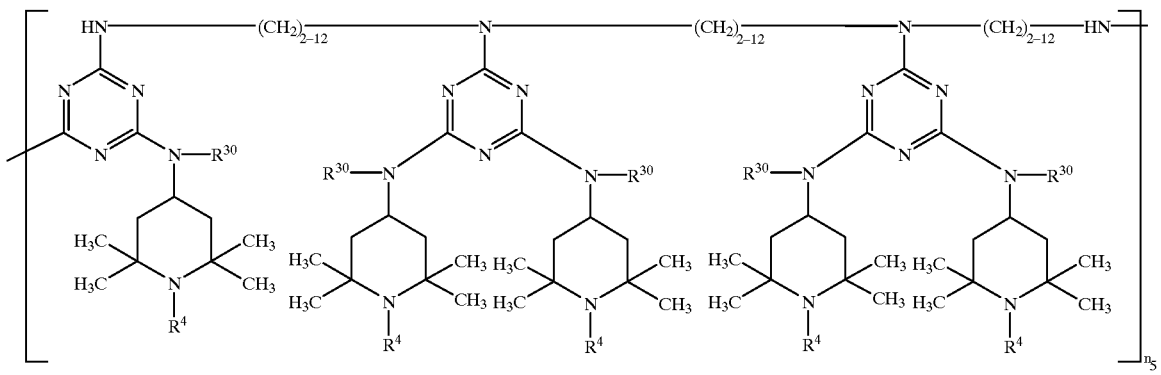
(B4-1)

-continued

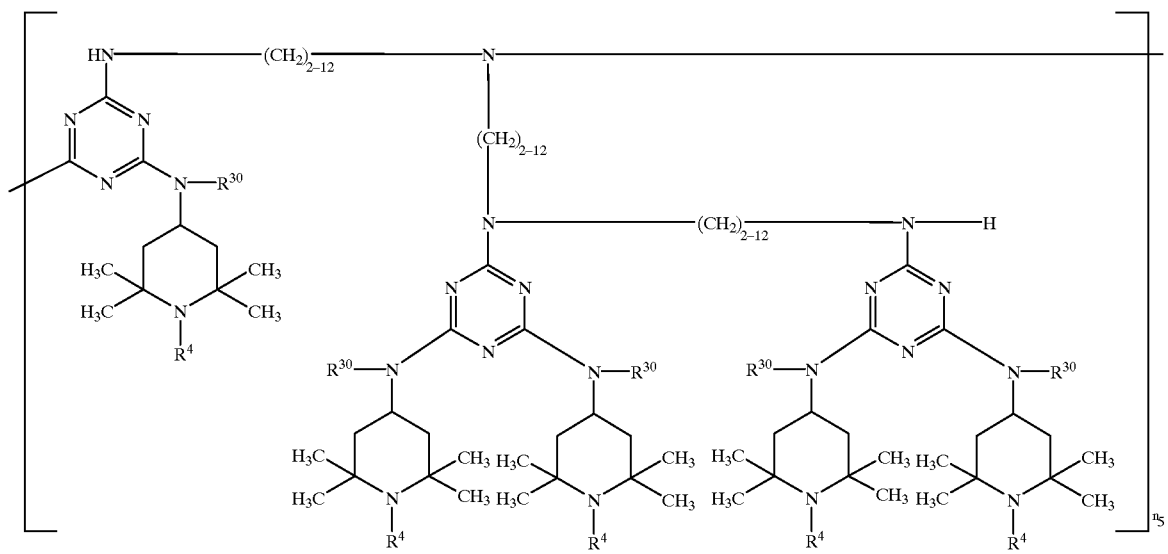
(B4-2)

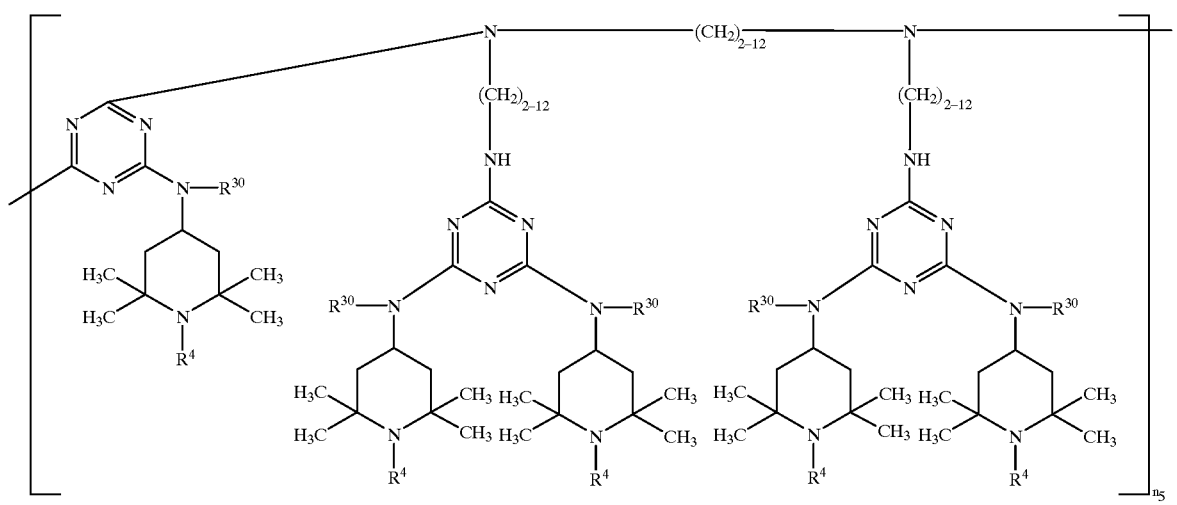
(B4-3)

or a mixture thereof, in which
$n_5$ is 1 to 20,
$R^4$ and $R^{30}$ are as defined above;

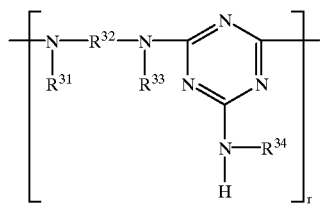
B5 where
r is as defined for formula B1,
$R^{31}$, $R^{33}$ and $R^{34}$ independently of one another are hydrogen, $C_1$–$C_{12}$-alkyl, $C_5$–$C_{12}$-cycloalkyl, $C_1$–$C_4$-alkyl-substituted $C_5$–$C_{12}$-cycloalkyl, phenyl, —OH— and/or $C_1$–$C_{10}$-alkyl-substituted phenyl, $C_7$–$C_9$-phenylalkyl, $C_7$–$C_9$-phenylkalkyl substituted on the phenyl radical by —OH and/or $C_1$–$C_{10}$-alkyl, or a group of the formula B5a

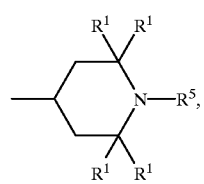
B5a where
$R^1$ and $R^5$ are as defined in claim 1, and
$R^{31}$ and $R^{33}$ in addition, independently of one another, are hydrogen, $R^{32}$ is $C_2$–$C_{18}$-alkylene, $C_5$–$C_7$-cycloalkylene or $C_1$–$C_4$-alkylenedi($C_5$–$C_7$-cycloalkylene) or the radicals $R^{31}$, $R^{32}$ and $R^{33}$, together with the nitrogen atoms to which they are attached, form a 5- to 10-membered heterocyclic ring, and where at least one of the radicals $R^{31}$, $R^{33}$ and $R^{34}$ is a group of the formula B5a;

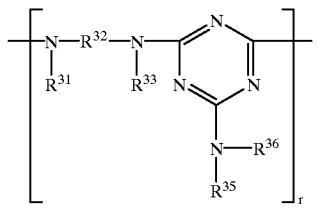

B6 in which $R^{31}$, $R^{32}$, $R^{33}$ and r are as defined above, $R^{35}$ and $R^{36}$ independently of one another can have the definition of $R^{34}$, or $R^{35}$ and $R^{36}$, together with the nitrogen atom to which they are attached, form a 5- to 10-membered heterocyclic ring which may in addition to the nitrogen heteroatom contain one or more other heteroatoms, preferably an oxygen atom, and at least one of the radicals $R^{31}$, $R^{33}$, $R^{35}$ and/or $R^{36}$ is a group of the formula (B5a);

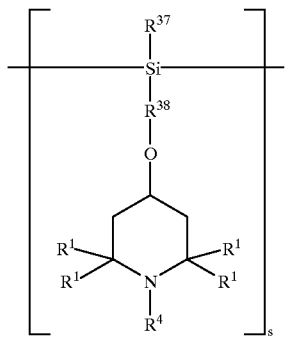

B7 where $R^1$ and $R^4$ are as defined in claim 1, s is as defined for formula B3, $R^{37}$ is $C_1$–$C_{10}$-alkyl, $C_5$–$C_{12}$-cycloalkyl, $C_1$–$C_4$-alkyl-substituted $C_5$–$C_{12}$-cycloalkyl, phenyl or $C_1$–$C_{10}$-alkyl-substituted phenyl, and $R^{38}$ is $C_3$–$C_{10}$-alkylene.

13. The mixture as claimed in claim 12, wherein n and m independently of one another are a number from 0 to 10, but n and m cannot both be 0, $R^1$ is hydrogen or a $C_1$–$C_4$-alkyl group, $R^2$ and $R^3$ independently of one another are a hydrogen atom or a $C_1$–$C_8$-alkyl group or, together with the carbon atom connecting them, are a 6- to 12-membered ring of carbon atoms or, together with the carbon atom connecting them, are a group of the formula (IV), $R^4$ and $R^5$ independently of one another are either hydrogen or a $C_1$–$C_5$-alkyl group, an oxygen radical O*, —OH, —NO, —CH$_2$CN, benzyl, allyl, a $C_1$–$C_{10}$-alkyloxy group, a $C_5$–$C_6$-cycloalkyloxy group, a $C_6$–$C_7$-aryloxy group, a $C_7$–$C_{10}$-arylalkyl group, a $C_3$–$C_6$-alkenyl group, a $C_3$–$C_6$-alkynyl group, a $C_1$–$C_4$-acyl group, halogen, or $C_7$–$C_9$-phenylalkyl which is unsubstituted or substituted on the phenyl ring by $C_1$–$C_2$-alkyl, $R^{13}$ is hydrogen or methyl, $R^{14}$ is $C_1$–$C_5$-alkylene, $R^{17}$, $R^{21}$ are hydrogen or $C_1$–$C_4$-alkyl, $R^{15}$, $R^{18}$ are a direct bond, $R^{16}$, $R^{20}$, are $C_1$–$C_{25}$-alkyl, phenyl, $R^{19}$ is hydrogen, $C_1$–$C_{12}$-alkyl or a group of the formula B2a, $R^{25}$, $R^{26}$, $R^{27}$, $R^{28}$ and $R^{29}$ independently of one another are a direct bond or $C_1$–$C_5$-alkylene, $R^{30}$ is hydrogen, $C_1$–$C_4$-alkyl, $C_5$–$C_6$-cycloalkyl or phenyl, $R^{31}$, $R^{33}$ and $R^{34}$ independently of one another are hydrogen, $C_1$–$C_{10}$-alkyl, $C_5$–$C_6$-cycloalkyl or a group of the formula B5a, $R^{32}$ is $C_2$–$C_{10}$-alkylene, $C_5$–$C_6$-cycloalkylene, $R^{35}$ and $R^{36}$ independently of one another are defined for $R^{34}$, or $R^{35}$ and $R^{36}$, together with the nitrogen atom to which they are attached, form a 5- to 7-membered heterocyclic ring which may also contain one or more heteroatoms, preferably an oxygen atom, and at least one of the radicals $R^{31}$, $R^{33}$, $R^{35}$ and/or $R^{36}$ is a group of the formula B5a, $R^{37}$ is $C_1$–$C_5$-alkyl, $C_5$–$C_6$-cycloalkyl or phenyl, $R^{38}$ is $C_3$–$C_5$-alkylene and $n_{5'}$, $n_{5''}$, $n_{5'''}$ are 2 to 4.

14. The mixture as claimed in claim 12, wherein n and m independently of one another are a number from 0 to 5, but n and m cannot both be 0, $R^1$ is methyl, $R^2$ and $R^3$, together with the carbon atom connecting them, are a 12-membered ring of carbon atoms or, together with the carbon atom connecting them, a group of the formula (IV), $R^4$ and $R^5$ independently of one another are hydrogen, acetyl, methyl, octyloxy or cyclohexyloxy, $R^{13}$ is hydrogen, $R^{14}$ is ethylene, $R^{17}$, $R^{21}$ are hydrogen or methyl, $R^{15}$, $R^{18}$ are a direct bond, $R^{16}$, $R^{20}$ are $C_1$–$C_{25}$-alkyl, phenyl, $R^{19}$ is a hexadecyl or a group of the formula B2a, $R^{25}$, $R^{27}$ are methylene, $R^{26}$ is a direct bond, $R^{28}$ is 2,2-dimethylethylene, $R^{29}$ is 1,1-dimethylethylene, $R^{30}$ is n-butyl, $R^{31}$, $R^{33}$ and $R^{34}$ independently of one another are isoctyl, cyclohexyl or 2,2,6,6-tetramethylpiperid-4-yl, and at least one of the radicals $R^{31}$, $R^{33}$ and $R^{34}$ must be 2,2,6,6-tetramethylpiperid-4-yl, $R^{32}$ is hexamethylene, $R^{35}$ and $R^{36}$ independently of one another are defined for $R^{34}$, or $R^{35}$ and $R^{36}$, together with the nitrogen atom to which they are attached, form a 6-membered heterocyclic ring which also contains an oxygen atom and so is morpholine, and at least one of the radicals $R^{31}$, $R^{33}$, $R^{35}$ and/or $R^{36}$ must be a radical 2,2,6,6-tetramethylpiperid-4-yl, $R^{37}$ is methyl,
$R^{38}$ is trimethylene, and
$n_{5'}$, $n_{5''}$, $n_{5'''}$ are 2 to 4.
15. A mixture as claimed in claim 12, wherein the polymeric HALS compounds in combination with compounds of the formula (III) are the following substances:
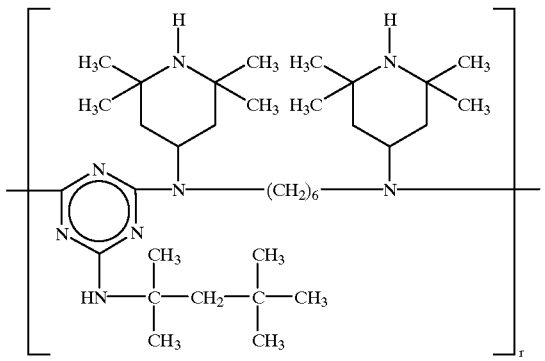
B'1
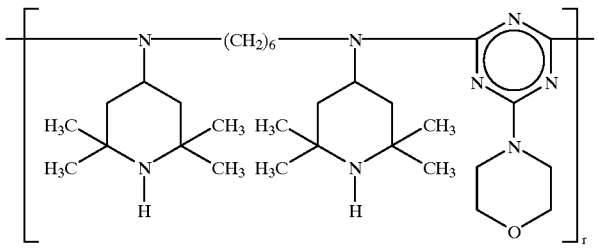
B'2
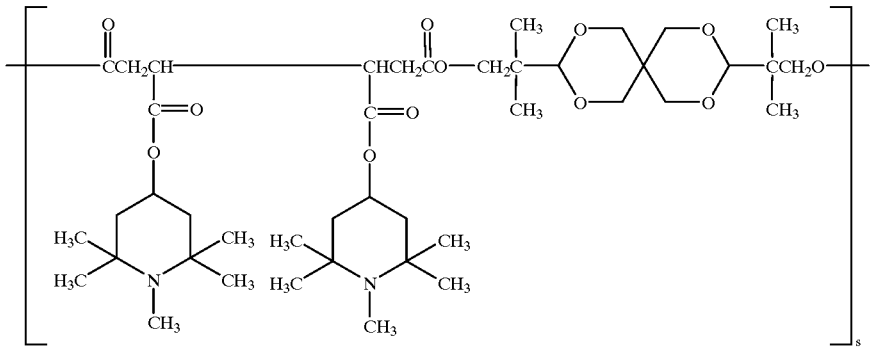
B'3
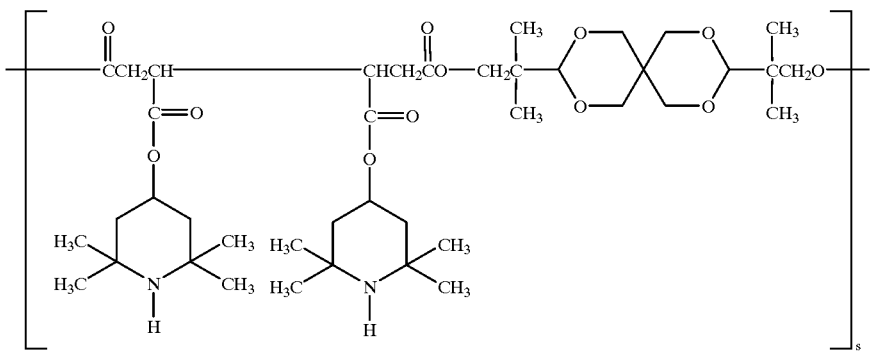
B'4
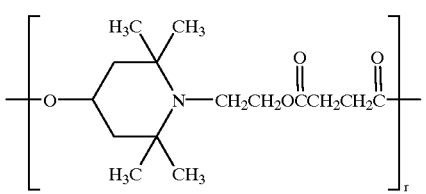
B'5

-continued
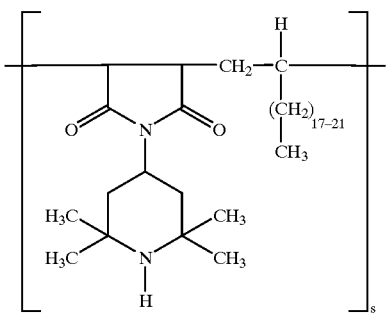
B'6
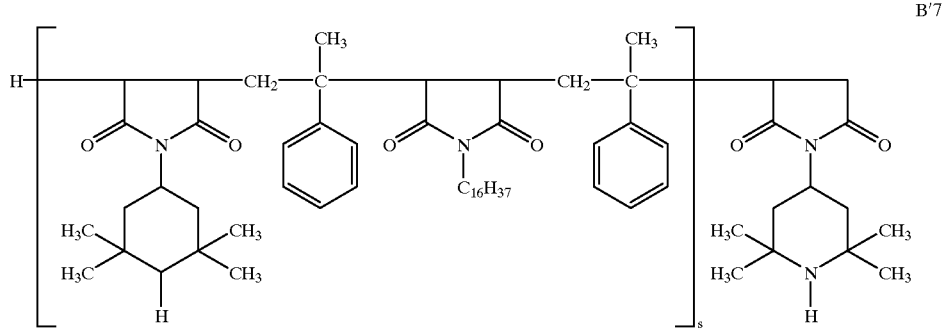
B'7
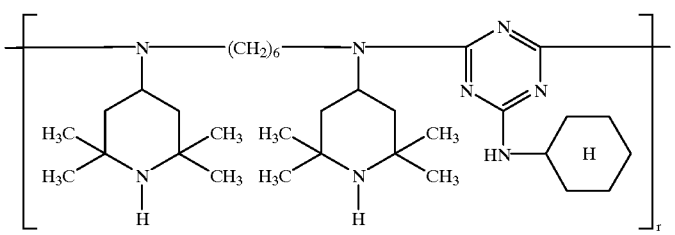
B'8
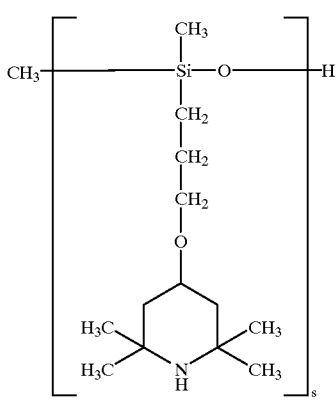
B'9
a product B'10 obtainable by reacting a polyamine of the formula B'10a:
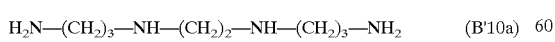 (B'10a)
with cyanuric chloride and then reacting the resulting product with a compound of the formula (B'10b)
(B'10b)
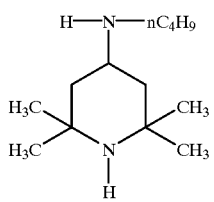
where B'10 is a compound of the formula B4-1', B4-2', B4-3'

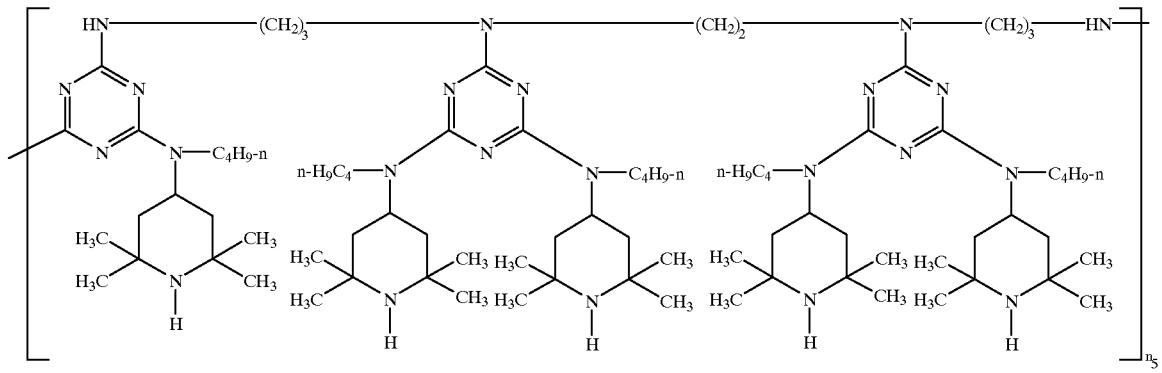
(B4-1′)
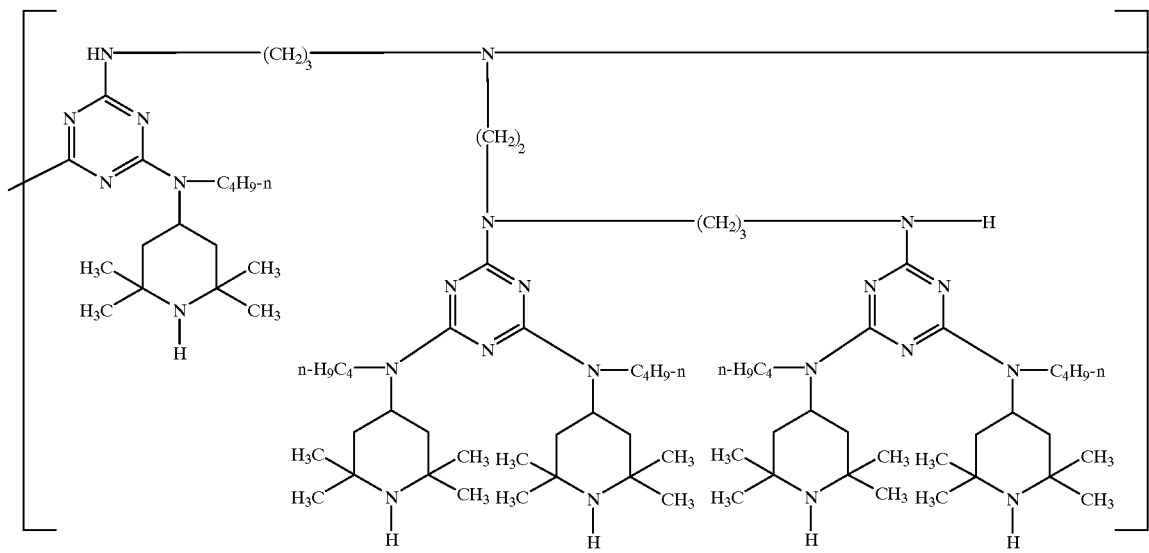
(B4-2′)
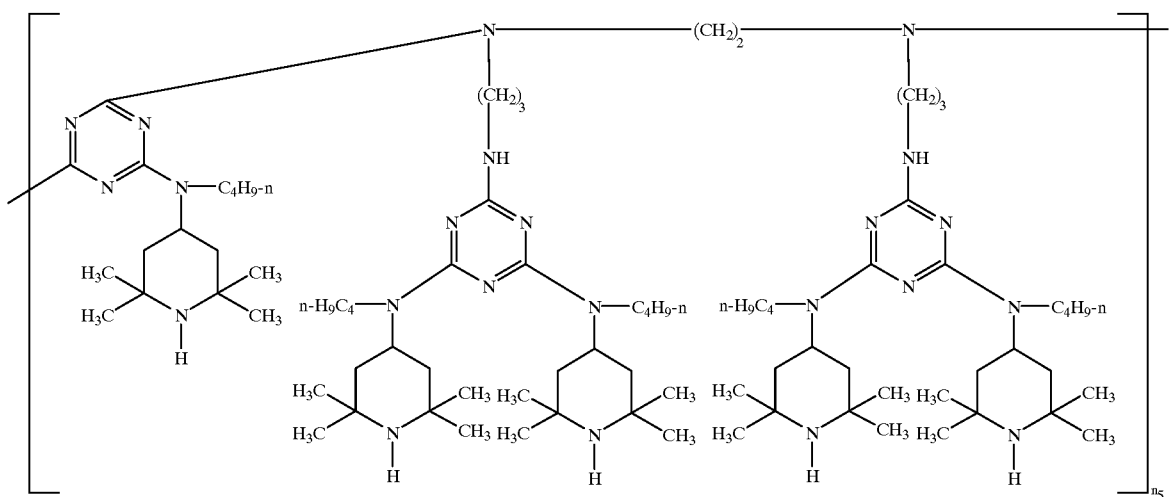
(B4-3′)

or a mixture thereof, where $n_5$ is 1 to 20.

16. A mixture of a compound of the formula (III) as claimed in claim 1 and one or more phosphorus stabilizers of the formulae C1 to C7

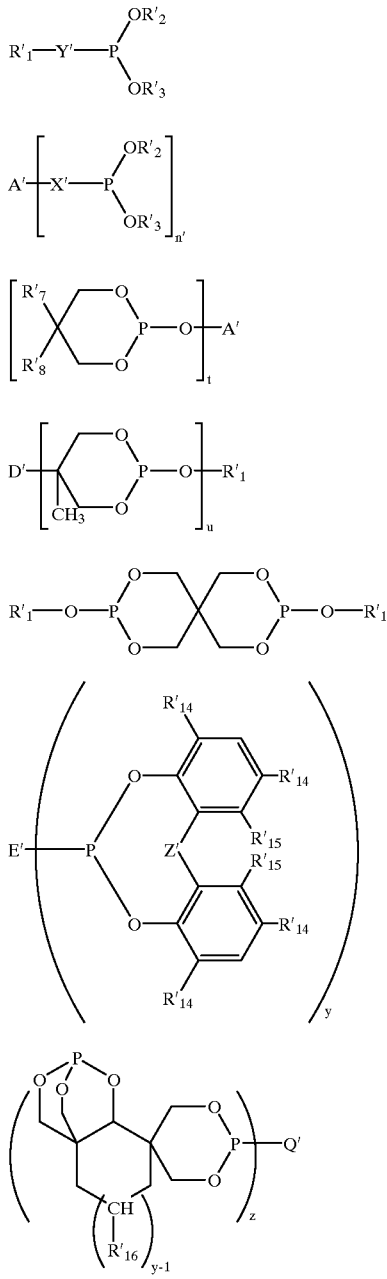

in which the indices are integral and n' is 2, 3 or 4;
u is 1 or 2;
t is 2 or 3;
y is 1, 2 or 3; and
z is 1 to 6;
A', if n' is 2, is alkylene of 2 to 18 carbon atoms, —S—, —O— or —NR'$_4$-interrupted alkylene of 2 to 12 carbon atoms; a radical of one of the formulae

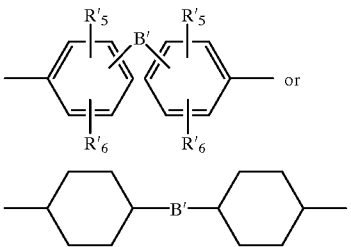

or phenylene;

A', if n' is 3, is a radical of the formula —C$_r$H$_{2r-1}$;
A', if n' is 4, is the radical of the formula

A" is as defined for A' if n' is 2;
B' is a radical of the formula —CH$_2$—; —CHR'$_4$—; —CR'$_1$R'$_4$—; —S— or a direct bond; or is C$_5$–C$_7$-cycloalkylidene; or is cyclohexylidene substituted in position 3, 4 and/or 5 by 1 to 4 C$_1$–C$_4$-alkyl radicals,
D', if u is 1, is methyl and, if u is 2, is —CH$_2$OCH$_2$—;
E', if y is 1, is alkyl of 1 to 18 carbon atoms, phenyl, a radical of the formula —OR'$_1$ or halogen;
E', if y is 2, is a radical of the formula O—A"—O—;
E', if y is 3, is a radical of the formula

or N(CH$_2$—CH$_2$—O—)$_3$,

Q' is the radical of an at least z-valent alcohol or phenol which is attached to the phosphorus atom(s) via the alcoholic and/or phenolic oxygen atom(s);
R'$_1$, R'$_2$ and R'$_3$ independently of one another are alkyl of 1 to 30 carbon atoms; halogen-, —COOR'$_4$—, —CN— or —CONR'$_4$R'$_4$-substituted alkyl of 1 to 18 carbon atoms; —S—, —O— or —NR'$_4$-interrupted alkyl of 2 to 18 carbon atoms; phenyl-C$_1$–C$_4$-alkyl; cycloalkyl of 5 to 12 carbon atoms; phenyl or naphthyl; phenyl or naphthyl substituted by halogen, 1 to 3 alkyl radicals or alkoxy radicals having in total 1 to 18 carbon atoms or phenyl-C$_1$–C$_4$-alkyl; or a radical of the formula

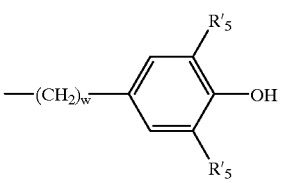

in which w is an integer from the range 3 to 6;
R'$_4$ or the radicals R'$_4$ independently of one another is or are hydrogen, alkyl of 1 to 18 carbon atoms, cycloalkyl of 5 to 12 carbon atoms, or phenylalkyl of 1 to 4 carbon atoms in the alkyl moiety;
R'$_5$ and R'$_6$ independently of one another are hydrogen, alkyl of 1 to 8 carbon atoms or cycloalkyl of 5 or 6 carbon atoms;

R'$_7$ and R'$_8$, if t=2, independently of one another are C$_1$–C$_4$-alkyl or together are a 2,3-dehydropentamethylene radical; and R'$_7$ and R'$_8$, if t=3, are methyl; the substituents R'$_{14}$ independently of one another are hydrogen, alkyl of 1 to 9 carbon atoms or cyclohexyl; the substituents R'$_{15}$ independently of one another are hydrogen or methyl; and R'$_{16}$ is hydrogen or C$_1$–C$_4$-alkyl and, if two or more radicals R'$_{16}$ are present, the radicals R'$_{16}$ are identical or different;

X' and Y' are each a direct bond or —O—; and

Z' is a direct bond; —CH$_2$—; —C(R'$_{16}$)$_2$— or —S—.

17. A stabilizer mixture as claimed in claim 16 comprising one or more phosphorus compounds of the formulae C'1 to C'12

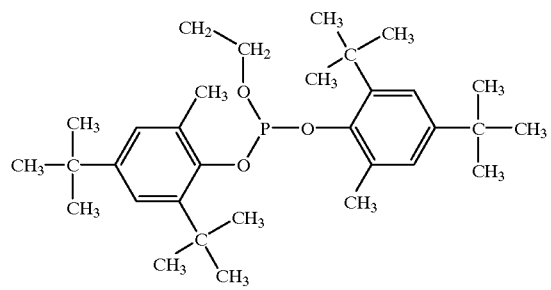

C'1

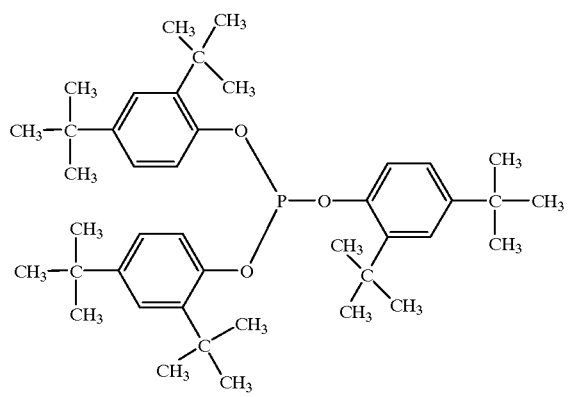

C'2

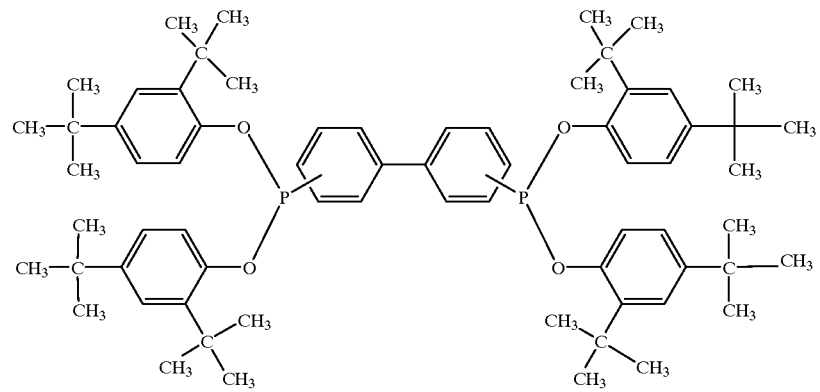

C'3

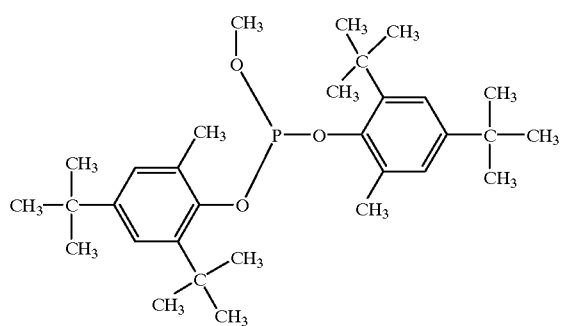
C'4
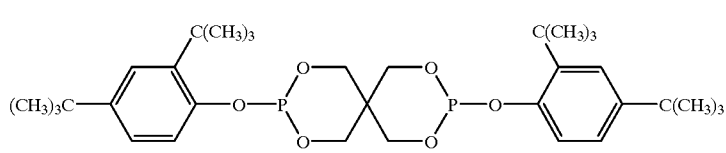
C'5
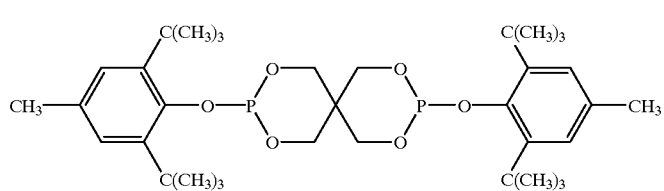
C'6
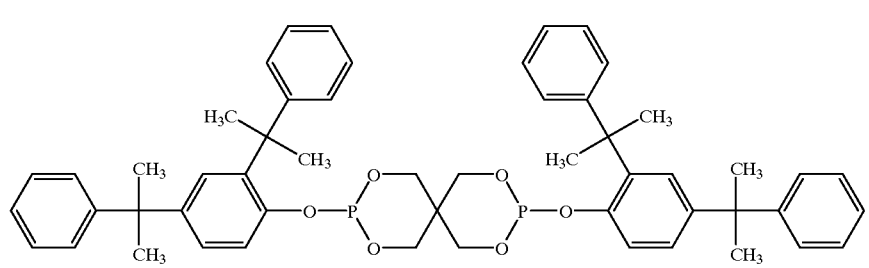
C'7
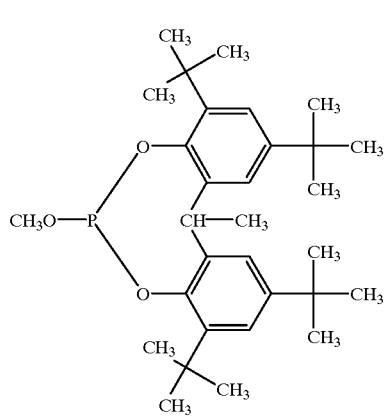
C'8

-continued

C'9

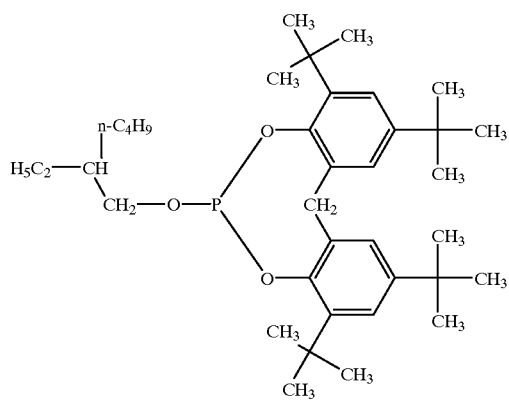

C'10

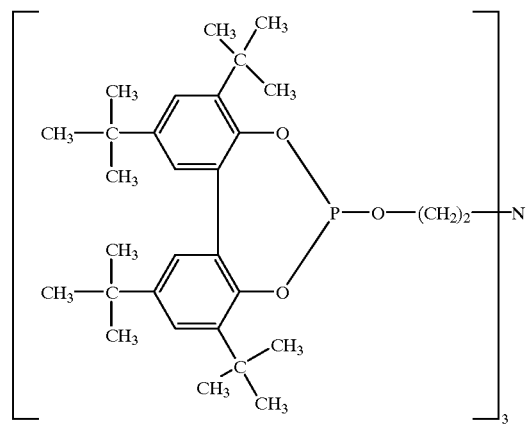

C'11

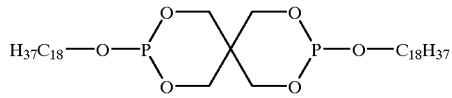

C'12

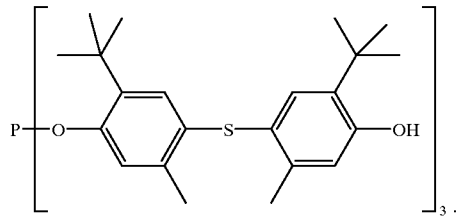

18. A mixture of a compound of the formula (III) as claimed in claim 1 and at least one UV absorber, wherein said UV absorber is 2-hydroxybenzophenone, 2-hydroxyphenylbenzotriazole, cinnamic acid derivative or oxyanilide.

19. A mixture as claimed in claim 8, wherein the proportion of compound of the formula (III) can be between 1 and 99% by weight.

20. A blend of a mixture as claimed in claim 8 and light stabilizers from the class of the UV absorbers.

21. A blend of compounds of the formula (III) as claimed in claim 1, alone or in mixtures as claimed in claims 8 to 18, and one or more N,N-dialkyl-substituted hydroxylamines.

22. A blend as claimed in claim 21, wherein the N,N-dialkyl-substituted hydroxylamine is N,N-dioctadecylhydroxylamine.

23. A mixture of a compound of the formula (III) as claimed in claim 1 with one or more basic or other acid-binding costabilizers, wherein the latter are selected from the group consisting of metal carboxylates, oxides, hydroxides and carbonates and/or zeolites and/or hydrotalcites.

24. A mixture as claimed in claim 23, wherein the costabilizers comprise calcium stearate and/or magnesium stearate and/or magnesium oxide and zinc oxide and/or carbonate-containing zinc oxide and/or hydrotalcites.

25. A mixture of a compound of the formula (III) as claimed in claim 1 with sterically hindered phenolic antioxidants.

26. A blend of a mixture as claimed in claim 8 with sterically hindered phenolic antioxidants.

27. A blend of a mixture as claimed in claim 26 with synergists of the 3-pyrazolidinone type.

28. A blend of a mixture as claimed in claim 26 with synergists of the 1,2,4-triazolidine-3,5-dione type.

29. A blend of a mixture as claimed in claim 26 with synergists of the 3-arylbenzofuran-2-one type.

30. A blend of a mixture as claimed in claim 26, wherein the 3-arylbenzofuran-2-one is 3-(3,4-dimethylphenyl)-5,7-di-tert-butyl-3H-benzofuran-2-one (formula D).

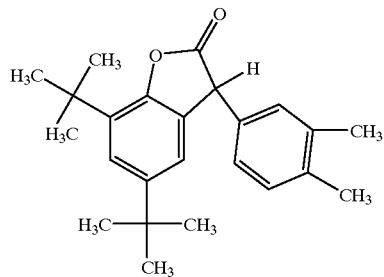

D

31. A blend of a mixture as claimed in claim 26 and basic or other acid-binding costabilizers.

32. A combination of a compound of the formula (III) as claimed in claim 1 and dyes or pigments based on organic or inorganic substances.

33. A method of using a mixture as claimed in claim 8 for stabilizing organic material, the method comprising adding the stabilizer in a concentration of 0.001 to 5% by weight, based on the stabilized organic material.

34. A stabilized organic material comprising a mixture as claimed in claim 8.

35. A stabilized organic material as claimed in claim 34, which is a polymer.

36. A stabilized organic material as claimed in claim 34, which comprises the compound (III) of the invention as claimed in claim 1 in a concentration of from 0.001 to 5% by weight, based on the stabilized organic material.

* * * * *